US012570685B2

(12) United States Patent
Seo et al.

(10) Patent No.: US 12,570,685 B2
(45) Date of Patent: Mar. 10, 2026

(54) 2-METHOXYESTRADIOL DERIVATIVES AND MEDICAL USES THEREOF

(71) Applicants: INSTITUT PASTEUR KOREA, Gyeonggi-Do (KR); KOREA INSTITUTE OF RADIOLOGICAL & MEDICAL SCIENCES, Seoul (KR)

(72) Inventors: Haeng Ran Seo, Seoul (KR); Inhee Choi, Seoul (KR); Junghwan Choi, Gyeonggi-do (KR); Young Mi Kim, Gyeonggi-do (KR); Yeonhwa Song, Seoul (KR); A-Ram Kim, Gyeonggi-do (KR); Yoon Jin Lee, Seoul (KR); Hae-June Lee, Seoul (KR); Jae-Kyung Nam, Seoul (KR); Jihee Kim, Seoul (KR); Su-Yeon Lee, Gyeonggi-do (KR)

(73) Assignees: INSTITUT PASTEUR KOREA, Gyeonggi-do (KR); KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 951 days.

(21) Appl. No.: 17/768,936

(22) PCT Filed: Oct. 14, 2020

(86) PCT No.: PCT/KR2020/014040

§ 371 (c)(1),
(2) Date: Apr. 14, 2022

(87) PCT Pub. No.: WO2021/075860

PCT Pub. Date: Apr. 22, 2021

(65) Prior Publication Data

US 2023/0295217 A1 Sep. 21, 2023

(30) Foreign Application Priority Data

Oct. 15, 2019 (KR) ........................ 10-2019-0127951

(51) Int. Cl.

| | |
|---|---|
| ***C07J 31/00*** | (2006.01) |
| ***A61P 1/16*** | (2006.01) |
| ***A61P 11/00*** | (2006.01) |
| ***C07J 1/00*** | (2006.01) |
| ***C07J 41/00*** | (2006.01) |

(52) U.S. Cl.

CPC ............... *C07J 1/0074* (2013.01); *A61P 1/16* (2018.01); *A61P 11/00* (2018.01); *C07J 1/007* (2013.01); *C07J 31/006* (2013.01); *C07J 41/0072* (2013.01)

(58) Field of Classification Search

CPC ....... C07J 1/007; C07J 1/0074; C07J 41/0072
See application file for complete search history.

(56) References Cited

U.S. PATENT DOCUMENTS

2005/0014737 A1 1/2005 Agoston et al.

FOREIGN PATENT DOCUMENTS

WO WO-2008/124878 A1 10/2008

OTHER PUBLICATIONS

Liu et al., Suppressive effects of 17beta-estradiol on hepatic fibrosis in CCI4-induced rat model. World J. Gastroenterol. vol. 10(9), pp. 1315-1320 (Year: 2004).*

International Search Report from corresponding PCT Application No. PCT/KR2020/014040, dated Feb. 22, 2021.

Suwandi, L. S., et al.; "Synthesis and antitumor activities of 3-modified 2-methoxyestradiol analogs", Bioorganic & medicinal chemistry letters, 2009, vol. 19, pp. 6459-6462.

Fang, Z., et al.; "Structure elucidation by synthesis of four metabolites of the antitumor drug ENMD-1198 detected in human plasma samples", Tetrahedron, 2009, vol. 65, pp. 10535-10543.

Hayashida, K., et al.; "17β-estradiol inhibits the production of infections particles of hepatitis C virus", Microbiology and immunology, 2010, vol. 54, pp. 684-690.

Tofovic S P et al, "2-methoxyestradiol attenuates bleomycin-induced pulmonary hypertension and fibrosis in estrogendeficient rats", Vascular Pharmacology, Elsevier, Amsterdam, NL, vol. 51, No. 2-3, Aug. 1, 2009 (Aug. 1, 2009), pp. 190-197.

Neamatallah Thikryat et al, "2-Methoxyestradiol attenuates liver fibrosis in mice: implications for M2 macrophages", Naunyn-Schmiedeberg's Archives of Pharmacology, Springer, DE, vol. 392, No. 3, Dec. 7, 2018 (Dec. 7, 2018), pp. 381-391.

Li Xingnan et al, "Improved profiling of estrogen metabolites by orbitrap LC/MS", Steroids, vol. 99, 2015, pp. 84-90.

Wang Qingqing et al, "Ultrasensitive quantification of serum estrogens in postmenopausal women and older men by liquid chromatography-tandem mass spectrometry", Steroids, vol. 96, Jan. 29, 2015 (Jan. 29, 2015), pp. 140-152.

Extended European Search Report from corresponding European Patent Application No. 20877958.7, dated Jan. 22, 2024.

* cited by examiner

*Primary Examiner* — Jeffrey S Lundgren
(74) *Attorney, Agent, or Firm* — Harness, Dickey & Pierce, P.L.C.

(57) ABSTRACT

The present invention relates to novel 2-Methoxyestradiol derivatives and their medical use. In particular, the novel derivatives of the present invention are useful for the treatment or prevention of liver or lung fibrosis. Accordingly, the present invention also provides medical uses of the 2-Methoxyestradiol derivatives of the present invention. The present invention also provides a method of treating or preventing liver or lung fibrosis comprising administering an effective amount of the 2-Methoxyestradiol derivatives of the present invention.

6 Claims, 2 Drawing Sheets

[Fig. 1]
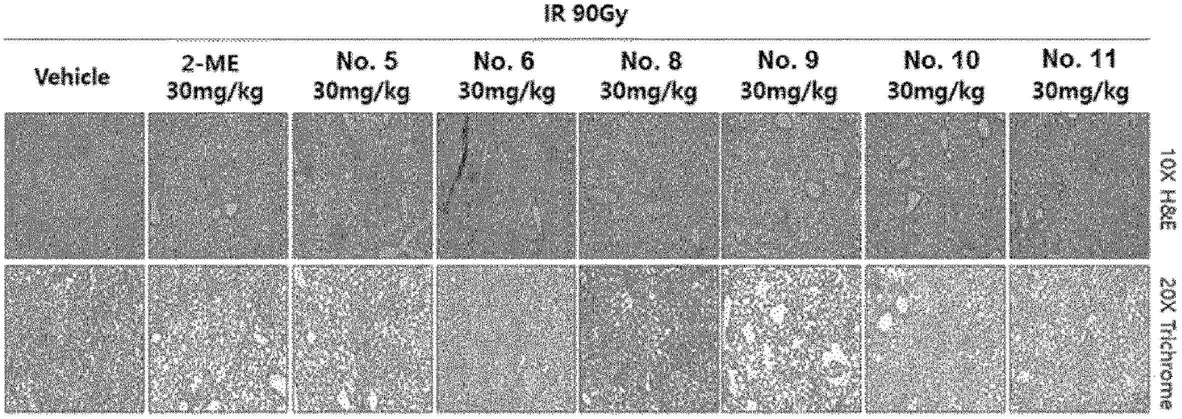
[Fig. 2]
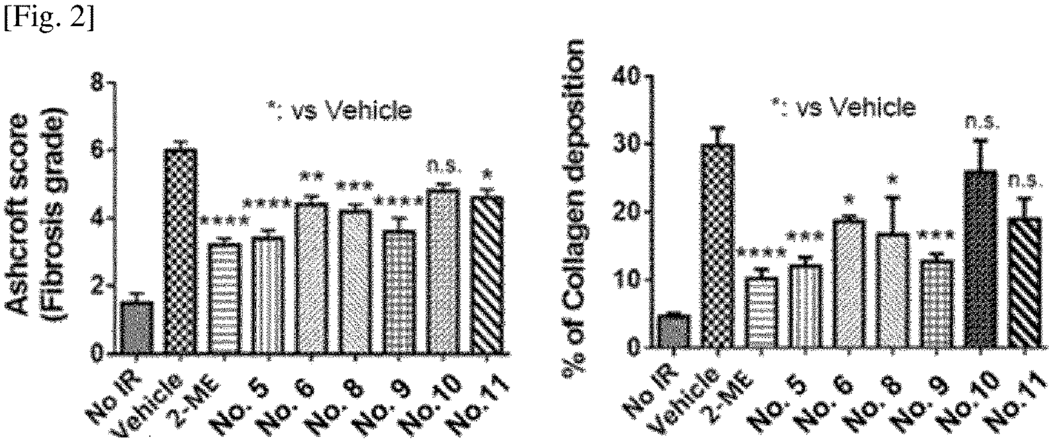
[Fig. 3]
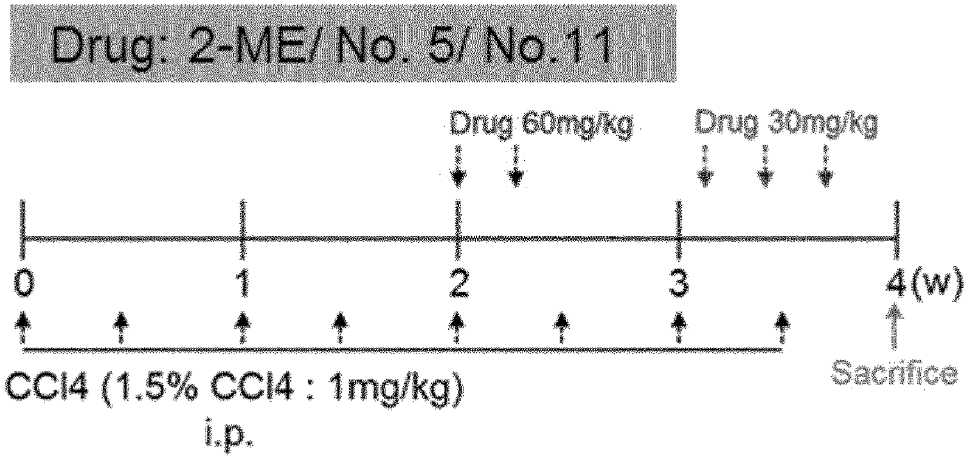

[Fig. 4]
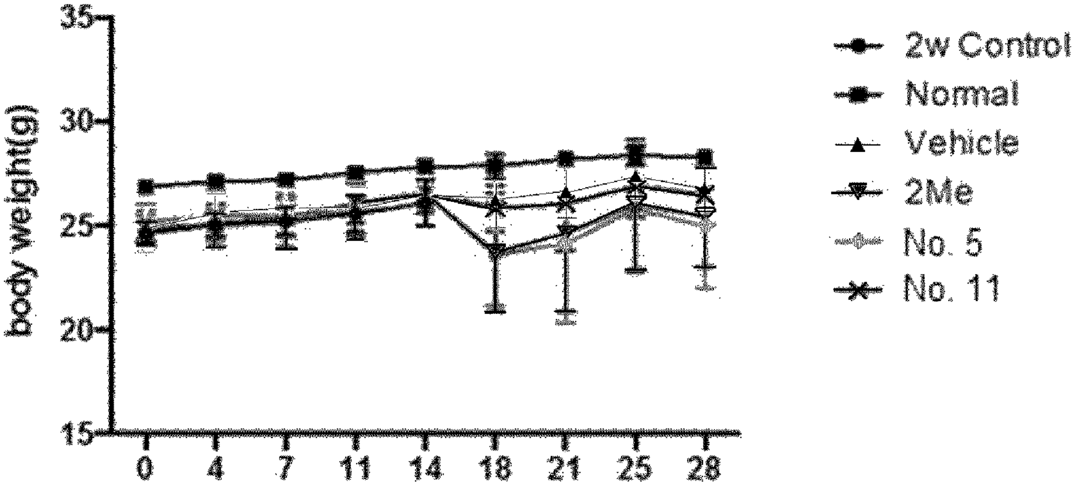
[Fig. 5]
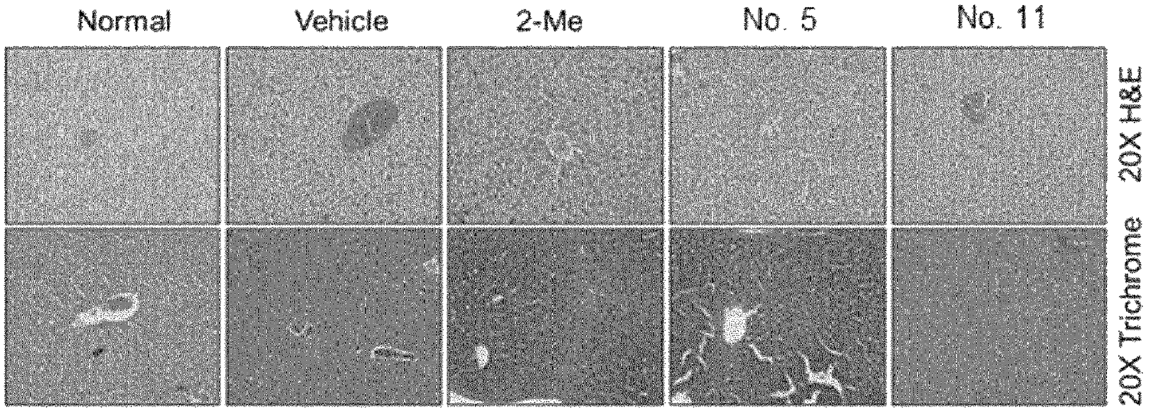
[Fig. 6]
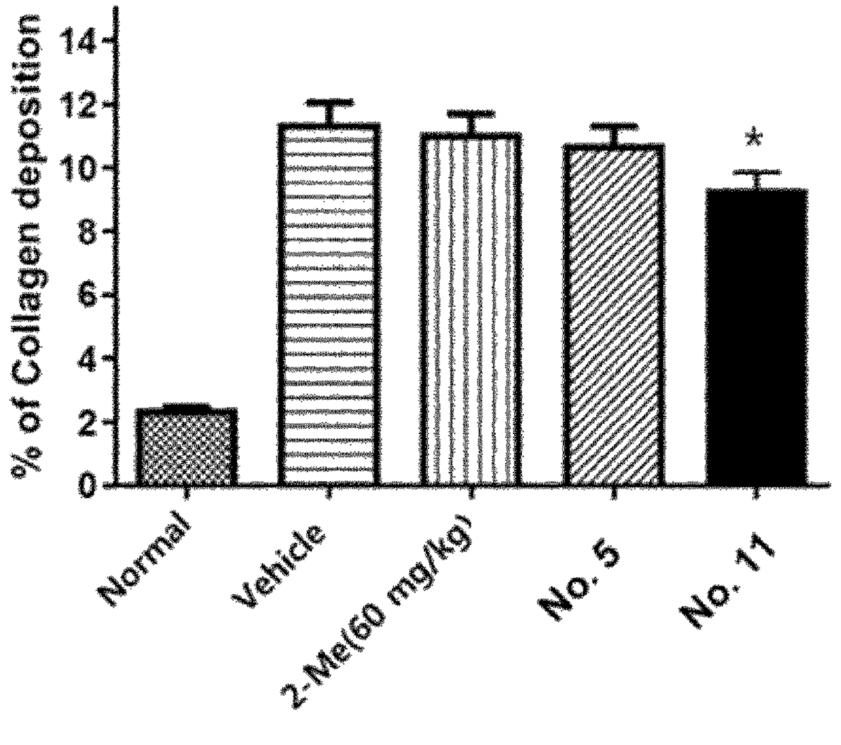

2-METHOXYESTRADIOL DERIVATIVES AND MEDICAL USES THEREOF

CROSS-REFERENCE TO RELATED APPLICATIONS

This application is a national phase application of PCT Application No. PCT/KR2020/014040, filed on Oct. 14, 2020, which claims the benefit and priority to Korean Patent Application No. 10-2019-0127951, filed on Oct. 15, 2019. The entire disclosures of the applications identified in this paragraph are incorporated herein by references.

TECHNICAL FIELD

The present disclosure relates to a group of compounds which are useful in treating or preventing liver or pulmonary fibrosis.

BACKGROUND ART

Fibrosis is the formation of excess fibrous connective tissue in an organ or tissue in a reparative or reactive process. Among fibrosis, liver or pulmonary fibrosis is an urgent disease required to be well treated.

Liver fibrosis is induced by severe inflammation and the excessive accumulation of ECM proteins. Because advanced liver fibrosis results in cirrhosis, it directly related high mortality of cirrhosis. Because liver transplantation may be the only treatment option for advanced liver fibrosis and cirrhosis, anti-fibrotic agents are keenly awaited. Despite liver fibrosis are highly prevalent disease, there are still no approved therapies because liver fibrosis has numerous causes and complications. The main causes of liver fibrosis are chronic hepatitis virus infection, alcohol abuse, drug-induced liver injury (DILI), cholestasis and NASH etc.

Pulmonary fibrosis refers to a condition in which fibrous connective tissue proliferates in the lungs, leading to destruction of normal lung structure and hardening and deterioration of lung tissues. In particular, idiopathic pulmonary fibrosis is a disease in which chronic inflammatory cells penetrate into the alveolar walls, causing various changes to harden the lung, causing severe structural changes in the lung tissue, and gradually deteriorating lung function. There is no effective treatment so far. In addition, radiotherapy is often used for patients with unresectable NSCLC tumors; however, it often cause radiation-induced pulmonary fibrosis (RIPF). To date, Roche's Esbriet (active ingredient: pirfenidone) and Boehringer Ingelheim's Ofev (active ingredient: nintedanib) are known to treat or improve these pulmonary fibrosis, but these drugs only slow the reduction of pulmonary function. Thus, there is a need to find a better drug.

DISCLOSURE OF INVENTION

Technical Problem

Thus one object of the present disclosure is to provide a compound which is useful in treating of preventing a fibrosis including liver and pulmonary fibrosis, pharmaceutical compositions comprising the compound as an active ingredient (effective agent), and medical-uses thereof for treating or preventing the fibrosis.

Another object of the present disclosure is to provide a method for treating or ameliorating a fibrosis including liver and pulmonary fibrosis comprising administering to a subject in need of treatment, amelioration or prevention of the fibrosis the compound according to the present disclosure.

SOLUTION TO PROBLEM

Summary

To achieve the object, in one embodiment, there is provided a compound of Chemical Formula 1:

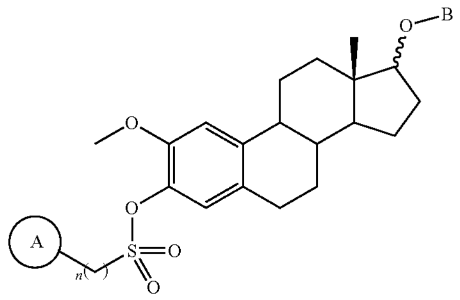

or a pharmaceutically acceptable salt thereof, in Chemical Formula 1, n is 0, 1, 2, or 3

A is a moiety selected from the group consisting of: phenyl, naphthyl, pyridyl, and pyrimidyl, wherein A is not substituted or optionally substituted with at least one substituent selected from the group consisting of halogen, $NO_2$, —O—$C_{1-4}$alkyl, OH, CN, $NH_2$, COOH, —$C_{1-4}$alkyl, -halo-$C_{1-4}$alkyl, —$C_{1-4}$haloalkoxy, phenyl, pyrrolyl, and pyrrolidinyl, B is H, —$S(O)_2$—$R^1$, —C(O)—$R^1$, or —OC(O)—$R^1$, and $R^1$ is phenyl, —$C_{1-4}$alkyl, naphthyl, $NH_2$, OH, or CN, wherein the phenyl, alkyl, and naphthyl of $R^1$ is not substituted or optionally substituted with at least one substituent selected from the group consisting of halogen, $NO_2$, —O—$C_{1-4}$alkyl, OH, CN, $NH_2$, COOH, phenyl, —$C_{1-4}$alkyl, -halo-$C_{1-4}$alkyl, and —$C_{1-4}$haloalkoxy.

In another embodiment, there is provided a pharmaceutical composition comprising a compound or pharmaceutically acceptable salt of Chemical Formula 1, and a pharmaceutically-acceptable carrier or additive.

In yet another embodiment, there is provided a method for treating a fibrosis comprising administering to a subject a therapeutically effective amount of a compound or pharmaceutically acceptable salt of Chemical Formula 1. The fibrosis includes, but is not limited to, liber fibrosis or pulmonary fibrosis. The compound or pharmaceutically acceptable salt of Chemical Formula according to the present disclosure is also useful in treating or preventing a fibrosis. That is, there is provided medical-uses of the compound or pharmaceutically acceptable salt of Chemical Formula 1 for treating the fibrosis such as liver fibrosis or pulmonary fibrosis.

The compounds, the pharmaceutical composition, and their medical use above are more fully described in the detailed description that follows.

Detailed Description

The following description is merely exemplary in nature and is not intended to limit the present disclosure, application, or uses.

Definitions

The generic terms used in the present disclosure are herein defined for clarity.

This specification uses the terms “substituent”, “radical”, “group”, “moiety”, and “fragment” interchangeably.

As used herein, the term “alkyl” means a saturated straight chain or branched non-cyclic hydrocarbon, unless the context clearly dictates otherwise, having from 1 to 10 carbon atoms. “lower alkyl” means alkyl having from 1 to 4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

As used herein, if the term “$C_1$-$C_6$” is used, it means the number of carbon atoms is from 1 to 6. For example, $C_1$-$C_6$ alkyl means an alkyl which carbon number is any integer of from 1 to 6.

The terms “halogen” and “halo” mean fluorine, chlorine, bromine or iodine.

As used herein, the term “haloalkyl”, “haloalkoxy”, “haloalkenyl” or “haloalkynyl” means an alkyl, alkoxy, alkenyl or alkynyl group, respectively, wherein one or more hydrogen atoms are substituted with halogen atoms. For example, the haloalkyl includes $-CF_3$, $-CHF_2$, $-CH_2$ , F, $-CBr_3$, $-CHBr_2$, $-CH_2Br$, $-CCl_3$, $-CHCl_2$, $-CH_2$, $CH_3$, CI, $-CI_3$, $-CHI_2$, $-CH_2I$, $-CH_2-CF_3$, $-CH_2-CHF_2$, $-CH_2-CH_2F$, $-CH_2-CBr_3$, $-CH_2-CHBr_2$, $-CH_2-CH_2Br$, $-CH_2-CCl_3$, $-CH_2-CHCl_2$, $-CH_2-CH_2CI$, —CH2-$CI_3$, $-CH_2-CHI_2$, $-CH_2-CH_2I$, and the like, wherein alkyl and halogen are as described above.

The term “hydroxyalkyl” means alkyl, wherein alkyl is as defined above, having one or more hydrogen atoms replaced with hydroxy, including $-CH_2OH$, $-CH_2CHOH$, —(CH) CHOH, $-(CH_2)_3CH_2OH$, $-(CH_2)_4CH_2OH$, $-(CH_2)_5CH_2OH$, —CH(OH)—$CH_3$, $-CH_2CH(OH)CH_3$, and the like.

As used herein, the term “substituted” means any of the above groups (i.e., alkyl, aryl, heteroaryl, heterocycle or cycloalkyl) wherein at least one hydrogen atom of the moiety being substituted is replaced with a substituent. In one embodiment, each carbon atom of the group being substituted is substituted with no more than two substituents. In another embodiment, each carbon atom of the group being substituted is substituted with no more than one substituent. In the case of a keto substituent, two hydrogen atoms are replaced with an oxygen which is attached to the carbon via a double bond. Unless specifically defined, substituents include halogen, hydroxyl, (lower) alkyl, haloalkyl, mono- or di-alkylamino, aryl, heterocycle, $-NO_2$, $-NR_aR_b$, $-NR_aC(=O)R_b$, $-NR_aC(=O)NR_aR_b$, $-NR_aC(=O)OR_b$, $-NR_aSO_2R_b$, $-OR_a$, —CN, $-C(=O)R_a$, $-C(=O)OR_a$, $-C(=O)NR_aR_b$, $-OC(=O)R_a$, $-OC(=O)OR_a$, $-OC(=O)NR_aR_b$, $-NR_aSO_2R_b$, $-PO_3R_a$, $-PO(OR_a)(OR_b)$, $-SO_2R_a$, $-S(O)R_a$, —SO (N)$R_a$ (e.g., sulfoximine), —$(R_a)S=NR_b$ (e.g., sulfilimine) and $-SR_a$, wherein $R_a$ and $R_b$ are the same or different and independently hydrogen, halogen, amino, alkyl, haloalkyl, aryl or heterocycle, or wherein $R_a$ and $R_b$ taken together with the nitrogen atom to which they are attached form a heterocycle. $R_a$ and $R_b$ may be in the plural based on atoms which those are attached to.

As used herein, the term “patient” means an animal, preferably a mammal such as a non-primate (e.g., cow, horse, sheep, pig, chicken, turkey, quail, cat, dog, mouse, rat, rabbit or guinea pig) or a primate (e.g. , monkey and human), most preferably a human.

As used herein, the term “pharmaceutically acceptable salt(s)” refers to a salt prepared from active compounds according to the present disclosure with relatively non-toxic acids or bases with active compounds, depending on the particular substituents of those compounds. When the compounds have a relatively acidic group, base-added salts can be obtained by contacting the neutral compounds with a sufficient amount of the desired base and a pure or inert solvent. Suitable pharmaceutically acceptable base addition salts include, but are not limited to sodium, sodium hydroxide, potassium, potassium hydroxide, calcium, calcium hydroxide, aluminum, organic amino, magnesium, magnesium hydroxide, zinc hydroxide, ammonia, arginine, benethamine, benzathine, choline, deanol, diethylamine, ethanolamine, ethylenediamine, glucamine, hydrabamine, imidazole, lysine, morpholine, piperazine, pyrrolidine, secondary maines, trimethylamine, tromethamine salts and the like. When the compounds have a relatively basic group, acid-added salts can be obtained by contacting the neutral compounds with a sufficient amount of the desired acid and pure or inert solvent. Suitable pharmaceutically acceptable acid addition salts include salts derived from non-toxic organic acids including, but are not limited to, acetic acid, propionic acid, isobutyl acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and the like, and non-toxic inorganic acids including, but are not limited to, hydrochloric acid, hydrobromic acid, nitric acid, carbonic acid, monohydrogencarbonic acid, phosphoric acid, monohydrogenphosphric acid, dihydrogenphosphoric acid, sulfuric acid, monohydrogensulfuric acid, hydrogen iodide, phosphorous acid and the like. Also it includes a salt of amino acid such as arginate or its analogues, and it also includes analogues of organic acid such as glucuronic or galacturonic acid. Some specific compounds of this disclosure have both basic and acidic functionality for the conversion of compounds with a basic or acidic portion (addition) salts.

As used herein, the term “effective amount” includes that amount of a compound of this disclosure sufficient to destroy, modify, control or remove the formation of excess fibrous connective tissue in an organ or tissue like liver or lung; delay or minimize the spread of excess fibrous connective tissue; or provide a therapeutic benefit in the treatment or management of fibrosis. As used herein, the term “prophylactically effective amount” refers to the amount of a compound sufficient to prevent the recurrence or spread of excess fibrous connective tissue or the occurrence of excess fibrous connective tissue in a patient.

As used herein, the term “prevention” includes the prevention of the recurrence, spread or onset of excess fibrous connective tissue in a patient.

As used herein, the term "treatment" includes the eradication, removal, modification, or control of excess fibrous connective tissue; and the minimizing or delay of the spread of excess fibrous connective tissue.

As used herein, the phrase "Compound(s) of this/the Disclosure" includes any compound(s) or pharmaceutically acceptable salt(s) of Chemical Formula 1, as well as clathrates, hydrates, solvates, or polymorphs thereof. And, even if the term "Compound(s) of the Disclosure" does not mention its pharmaceutically acceptable sat, the term includes salts thereof. In one embodiment, the compounds of this disclosure include stereo-chemically pure compounds, e.g., those substantially free (e.g., greater than 85% ee, greater than 90% ee, greater than 95% ee, greater than 97% ee, or greater than 99% ee) of other stereoisomers.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

As used herein, the term "purified" means that when isolated, the isolate is greater than 90% pure, in one embodiment greater than 95% pure, in another embodiment greater than 99% pure and in another embodiment greater than 99.9% pure.

The term "pharmaceutically-acceptable" means suitable for use in pharmaceutical preparations, generally considered as safe for such use, officially approved by a regulatory agency of a national or state government for such use, or being listed in South Korea or the U. S. Pharmacopoeia or other generally recognized pharmacopoeia for use in animals, and more particularly in humans.

Compounds of the Present Disclosure

There is provided a compound of Chemical Formula 1:

[Chemical Formula 1]

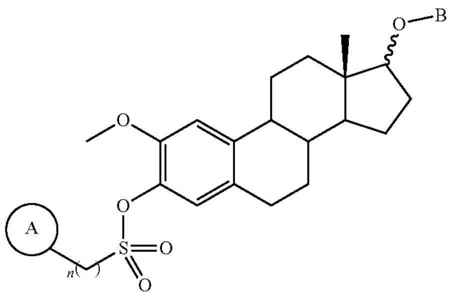

or a pharmaceutically acceptable salt thereof, in Chemical Formula 1, n is 0, 1, 2, or 3

A is a moiety selected from the group consisting of: phenyl, naphthyl, pyridyl, and pyrimidyl, wherein A is not substituted or optionally substituted with at least one substituent selected from the group consisting of halogen, $NO_2$, —O—$C_{1-4}$alkyl, OH, CN, $NH_2$, COOH, —$C_{1-4}$ alkyl, -halo-$C_{1-4}$ alkyl, —$C_{1-4}$ haloalkoxy, phenyl, pyrrolyl, and pyrrolidinyl, B is H, —$S(O)_2$—$R^1$, —C(O)—$R^1$, or —OC(O)—$R^1$, and $R^1$ is phenyl, —$C_{1-4}$ alkyl, naphthyl, $NH_2$, OH, or CN, wherein the phenyl, alkyl, and naphthyl of $R^1$ is not substituted or optionally substituted with at least one substituent selected from the group consisting of halogen, $NO_2$, —O—$C_{1-4}$alkyl, OH, CN, $NH_2$, COOH, phenyl, —$C_{1-4}$alkyl, -halo-$C_{1-4}$alkyl, and —$C_{1-4}$haloalkoxy.

In another embodiment, in the Chemical Formula 1, n is 0, 1, or 2,

A is a moiety selected from the group consisting of: phenyl, naphthyl, and pyridyl, wherein A is not substituted or optionally substituted with at least one substituent selected from the group consisting of halogen, $NO_2$, —O—$C_{1-4}$alkyl, OH, CN, $NH_2$, COOH, —$C_{1-4}$ alkyl, -halo-$C_{1-4}$ alkyl, phenyl, pyrrolyl, and pyrrolidinyl, B is H, —$S(O)_2$—$R^1$, or —C(O)—$R^1$, and $R^1$ is phenyl, —$C_{1-4}$ alkyl, naphthyl, $NH_2$, OH, or CN, wherein the phenyl, alkyl, and naphthyl of $R^1$ is not substituted or optionally substituted with at least one substituent selected from the group consisting of halogen, $NO_2$, —O—$C_{1-4}$alkyl, OH, CN, $NH_2$, COOH, —$C_{1-4}$alkyl, and -halo-$C_{1-4}$ alkyl.

Preferably, in yet another embodiment, in the Chemical Formula 1, n is 0, 1, or 2, A is phenyl or naphthyl, wherein A is not substituted or optionally substituted with at least one substituent selected from the group consisting of halogen, $NO_2$, —O—$C_{1-4}$ alkyl, and OH, B is H, —$S(O)_2$—$R^1$, or —C(O)—$R^1$, and $R^1$ is phenyl, —$C_{1-4}$alkyl, naphthyl, or $NH_2$, wherein the phenyl, alkyl, and naphthyl of $R^1$ is not substituted or optionally substituted with at least one halogen.

The inventors had synthesized and evaluated lots of compounds to find out compounds that are useful in treating or preventing a fibrosis. Finally, the compounds of the present disclosure are identified to be suitable for the object of the present disclosure. The compounds of the present disclosure have a very good effects on preventing, inhibiting or alleviating pulmonary or liver fibrosis.

Non-limiting examples of the compounds of the present disclosure include the compounds of Table 1 below and pharmaceutically acceptable salts thereof.

TABLE 1

| No. | Structure | Name |
|---|---|---|
| 1 | 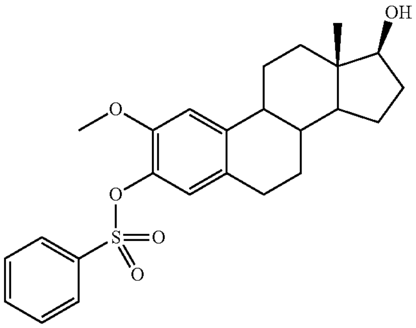 [SMILES: COc1cc2c(cc1OS(=O)(=O)c1ccccc1)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl benzenesulfonate |
| 2 | 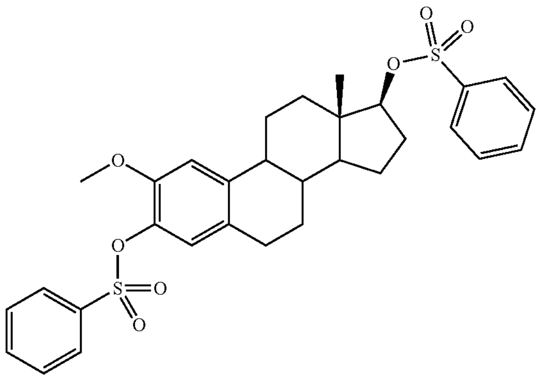 [SMILES: COc1cc2c(cc1OS(=O)(=O)c1ccccc1)CCC1C2CC[C@@]2(C)C1CC[C@@H]2OS(=O)(=O)c1ccccc1] | (13S,17S)-2-methoxy-13-methyl-7,8,9,11,12,13,14,15,16,17-decahydro-6H-cyclopenta[a]phenanthrene-3,17-diyl dibenzenesulfonate |
| 3 | 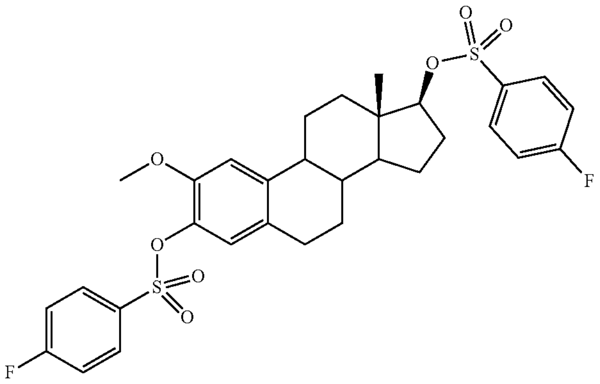 [SMILES: COc1cc2c(cc1OS(=O)(=O)c1ccc(F)cc1)CCC1C2CC[C@@]2(C)C1CC[C@@H]2OS(=O)(=O)c1ccc(F)cc1] | 13S,17S)-2-methoxy-13-methyl-7,8,9,11,12,13,14,15,16,17-decahydro-6H-cyclopenta[a]phenanthrene-3,17-diyl bis(4-fluorobenzenesulfonate) |

TABLE 1-continued

| No. | Structure | Name |
|---|---|---|
| 4 | 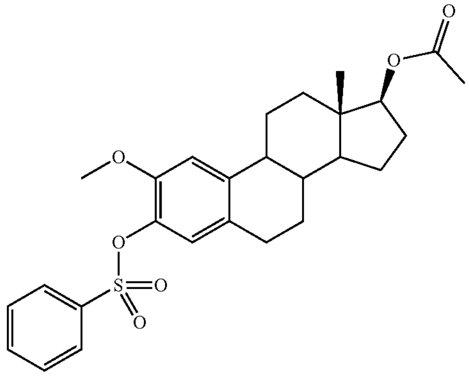 [SMILES: COc1cc2c(cc1OS(=O)(=O)c1ccccc1)CCC1C2CC[C@@]2(C)C1CC[C@@H]2OC(C)=O] | (13S,17S)-2-methoxy-13-methyl-3-((phenylsulfonyl)oxy)-7,8,9,11,12,13,14,15,16,17-decahydro-6H-cyclopenta[a]phenanthren-17-yl acetate |
| 5 | 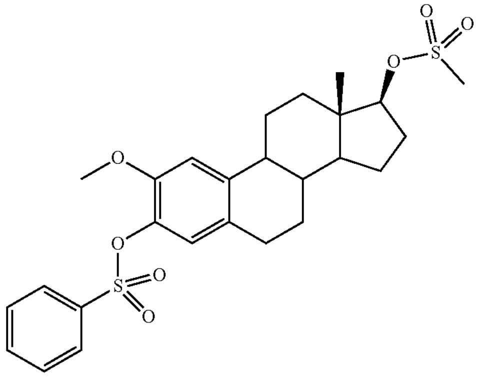 [SMILES: COc1cc2c(cc1OS(=O)(=O)c1ccccc1)CCC1C2CC[C@@]2(C)C1CC[C@@H]2OS(C)(=O)=O] | (13S,17S)-2-methoxy-13-methyl-17-((methylsulfonyl)oxy)-7,8,9,11,12,13,14,15,16,17-decahydro-6H-cyclopenta[a]phenanthren-3-yl benzenesulfonate |
| 6 | 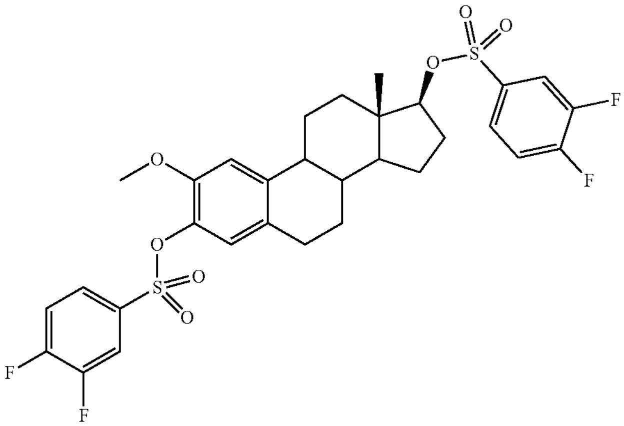 [SMILES: COc1cc2c(cc1OS(=O)(=O)c1ccc(F)c(F)c1)CCC1C2CC[C@@]2(C)C1CC[C@@H]2OS(=O)(=O)c1ccc(F)c(F)c1] | (13S,17S)-2-methoxy-13-methyl-7,8,9,11,12,13,14,15,16,17-decahydro-6H-cyclopenta[a]phenanthrene-3,17-diyl bis(3,4-difluorobenzenesulfonate) |
| 7 | 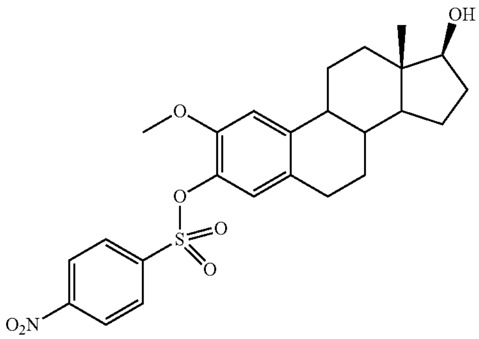 [SMILES: COc1cc2c(cc1OS(=O)(=O)c1ccc([N+](=O)[O-])cc1)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl 4-nitrobenzenesulfonate |

TABLE 1-continued

| No. | Structure | Name |
| --- | --- | --- |
| 8 | 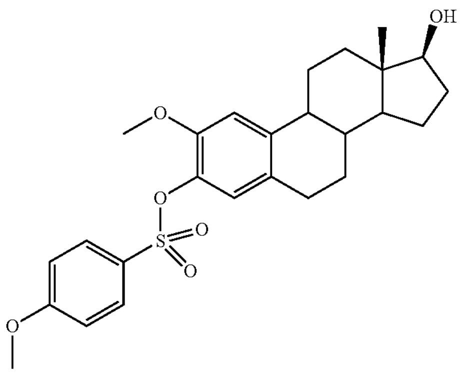 [SMILES: COc1ccc(S(=O)(=O)Oc2cc3c(cc2OC)C2CC[C@@]4(C)C(CC[C@@H]4O)C2CC3)cc1] | (13S,17S)-17-hydroxy-2-methoxy-13-methyl-7,8,9,11,12,13,14,15,16,17-decahydro-6H-cyclopenta[a]phenanthren-3-yl 4-methoxybenzenesulfonate |
| 9 | 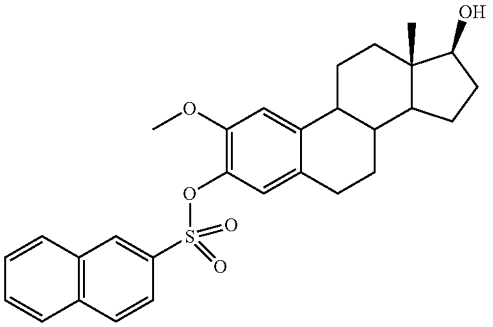 [SMILES: COc1cc2c(cc1OS(=O)(=O)c1ccc3ccccc3c1)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl naphthalene-2-sulfonate |
| 10 | 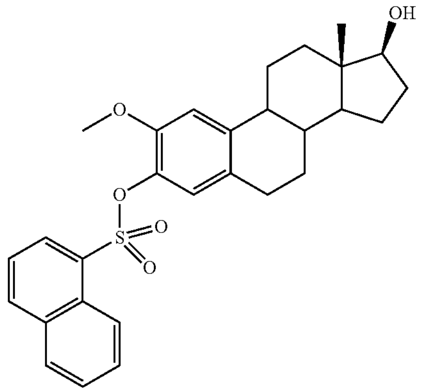 [SMILES: COc1cc2c(cc1OS(=O)(=O)c1cccc3ccccc13)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl naphthalene-1-sulfonate |
| 11 | 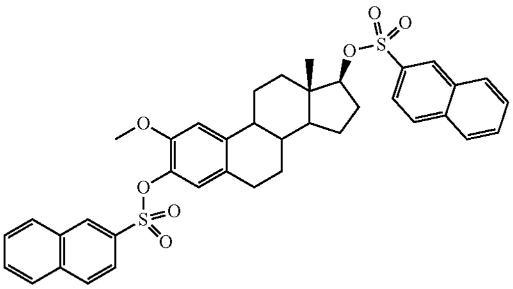 [SMILES: COc1cc2c(cc1OS(=O)(=O)c1ccc3ccccc3c1)CCC1C2CC[C@@]2(C)C1CC[C@@H]2OS(=O)(=O)c1ccc2ccccc2c1] | (13S,17S)-2-methoxy-13-methyl-7,8,9,11,12,13,14,15,16,17-decahydro-6H-cyclopenta[a]phenanthrene-3,17-diyl bis(naphthalene-2-sulfonate) |

TABLE 1-continued

| No. | Structure | Name |
| --- | --- | --- |
| 12 | 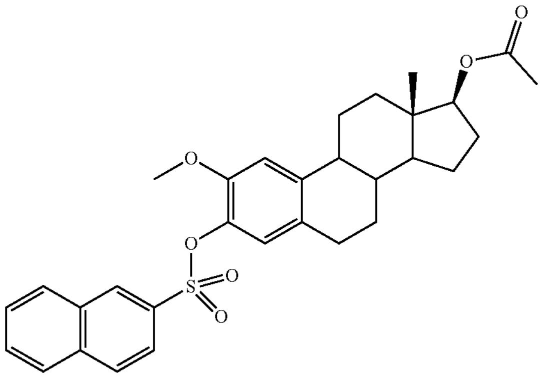 [SMILES: COc1cc2c(cc1OS(=O)(=O)c1ccc3ccccc3c1)CCC1C2CC[C@@]2(C)C1CC[C@@H]2OC(C)=O] | (13S,17S)-2-methoxy-13-methyl-3-((naphthalen-2-ylsulfonyl)oxy)-7,8,9,11,12,13,14,15,16,17-decahydro-6H-cyclopenta[a]phenanthren-17-yl acetate |
| 13 | 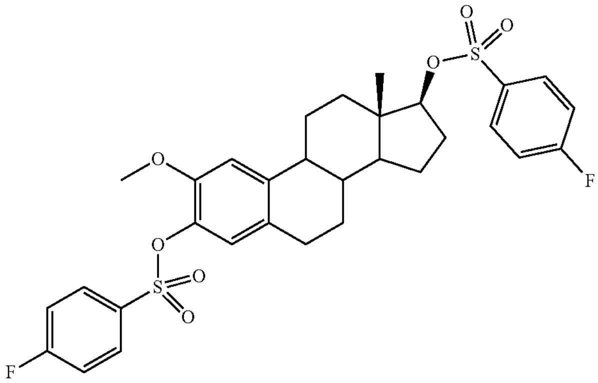 [SMILES: COc1cc2c(cc1OS(=O)(=O)c1ccc(F)cc1)CCC1C2CC[C@@]2(C)C1CC[C@@H]2OS(=O)(=O)c1ccc(F)cc1] | (13S,17S)-2-methoxy-13-methyl-7,8,9,11,12,13,14,15,16,17-decahydro-6H-cyclopenta[a]phenanthrene-3,17-diyl bis(4-fluorobenzenesulfonate) |
| 14 | 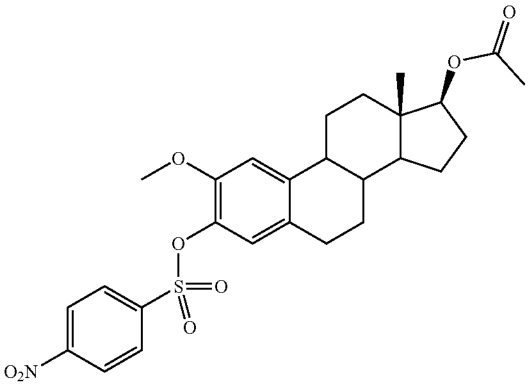 [SMILES: COc1cc2c(cc1OS(=O)(=O)c1ccc([N+](=O)[O-])cc1)CCC1C2CC[C@@]2(C)C1CC[C@@H]2OC(C)=O] | (13S,17S)-2-methoxy-13-methyl-3-(((4-nitrophenyl)sulfonyl)oxy)-7,8,9,11,12,13,14,15,16,17-decahydro-6H-cyclopenta[a]phenanthren-17-yl acetate |
| 15 | 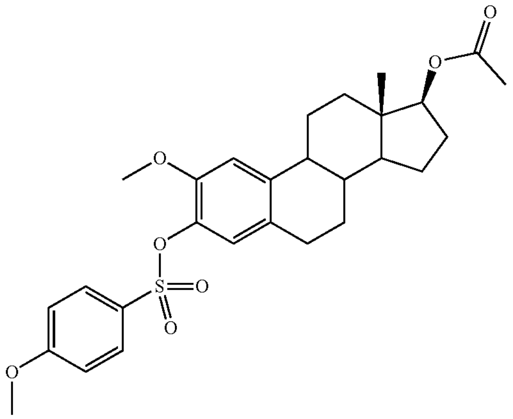 [SMILES: COc1ccc(S(=O)(=O)Oc2cc3c(cc2OC)C2CC[C@@]4(C)C(CC[C@@H]4OC(C)=O)C2CC3)cc1] | (13S,17S)-2-methoxy-3-(((4-methoxyphenyl)sulfonyl)oxy)-13-methyl-7,8,9,11,12,13,14,15,16,17-decahydro-6H-cyclopenta[a]phenanthren-17-yl acetate |

Preferably, in yet another embodiment, the present disclosure provides (13S,17S)-17-hydroxy-2-methoxy-13-methyl-7,8,9,11,12,13,14,15,16,17-decahydro-6H-cyclopenta[a]phenanthren-3-yl benzenesulfonate, (13S,17S)-2-methoxy-13-methyl-7,8,9,11,12,13,14,15,16,17-decahydro-6H -cyclopenta[a]phenanthrene-3,17-diyldibenzenesulfonate, (13S,17S)-2-methoxy-13-methyl-17-((methylsulfonyl)oxy)-7,8,9,11,12,13,14,15,16,1 7-decahydro-6H-cyclopenta[a]phenanthren-3-yl benzenesulfonate, (13S,17S)-2-methoxy-13-methyl-7,8,9,11,12,13,14,15,16,17-decahydro-6H -cyclopenta[a]phenanthrene-3,17-diyl bis(naphthalene-2-sulfonate), or a pharmaceutically acceptable salt thereof.

The above four compounds and their pharmaceutically acceptable salts are very suitable for the object of the present disclosure.

In yet another embodiment, there is provided a pharmaceutical composition comprising a therapeutically effective amount of a compound or pharmaceutically acceptable salt of Chemical Formula 1, and a pharmaceutically acceptable carrier.

In another embodiment, there is provided a method for treating or preventing a fibrosis comprising administering to a subject in need thereof a therapeutically effective amount of a compound or pharmaceutically acceptable salt of Chemical Formula 1. The fibrosis includes, but is not limited to, liver fibrosis or pulmonary fibrosis. The liber fibrosis includes, but is not limited to, a fibrosis caused by chronic hepatitis virus infection, alcohol abuse, drug-induced liver injury (DILI), cholestasis, or NASH (Non-Alcoholic Steath Hepatitis). The pulmonary fibrosis includes, but is not limited to, radiation-induced pulmonary fibrosis, or idiopathic pulmonary fibrosis. In another embodiment, the subject is a human.

That is, there is provided a medical use of Chemical Formula 1 or pharmaceutically acceptable salt thereof, wherein Chemical Formula 1 or pharmaceutically acceptable salt thereof is used as an effective agent. In one embodiment, the medical-use is for treatment or prevention of the fibrosis described above.

There also is provided a method for treating or preventing the fibrosis described above comprising administering to a subject in need thereof a therapeutically effective amount of a compound of Chemical Formula 1, or pharmaceutically acceptable salt thereof.

The compounds of the present disclosure are generally administered in a therapeutically effective amount.

The compounds of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains.

Pharmaceutical Compositions, Dosage Forms and Administration Routes

For the treatment of the diseases or conditions referred to the above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intra-arterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and isotonic agents.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

References for Preparing Pharmaceutical Compositions

Methods for preparing pharmaceutical compositions for treating or preventing a disease or condition are well known in the art to which the present disclosure pertains. For example, based on Remington : the science and practice of pharmacy ($22^{nd}$ ed., Pharmaceutical Press 2013), pharmaceutically acceptable excipients, carriers, additives and so on can be selected and then mixed with the compounds of the present disclosure for making the pharmaceutical compositions.

Advantageous Effects of Invention

The present disclosure provides a compound which is useful in treating or preventing a fibrosis, a pharmaceutical composition having the compound as an effective agent, a medical use, particularly for treating or preventing a fibrosis, of the compound, and a method of treatment comprising administering the compound to a subject in need of such treatment or prevention.

BRIEF DESCRIPTION OF DRAWINGS

FIGS. 1 and 2 show validation results of in vivo efficacy of 2-ME derivatives on the RIPF. Representative images of hematoxylin and eosin stained lung sections from mice are shown at 2 weeks after irradiation. Lung sections were stained with Masson's Trichrome stain to visualize blue-colored collagen deposition and quantitative assessments of the degree of collagen deposition were determined (*p<0.05, p<0.01, *p<0.001, ****p<0.0001, ns not significant vs vehicle).

FIGS. 3 to 6 show validation results of in vivo efficacy of 2-ME derivatives on the liver fibrosis.

In the FIGS. 1 to 6, No. means number of compounds listed in the Tables 3 and 4.

MODE FOR THE INVENTION

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all of its material advantages.

Abbreviations and symbols utilized herein are in accordance with the common usage of such abbreviations and symbols by those skilled in the chemical and biological arts. Specifically, the following abbreviations may be used in the examples and throughout the specification.

RIPF (Radiation-Induced Pulmonary Fibrosis)
NASH (Non-Alcoholic Steath Hepatitis)
ECM (ExtraCellular Matrix)
2-ME (2-Methoxyestradiol)
EndMT (Endothelial-to-mesenchymal transition)
HUVECs (Human Umbilical Vein Endothelial Cells)
g (grams) mg (milligrams)
kg (kilograms) μg (micrograms)
L (liters) mL (milliliters)
μL (microliters) rt (room temperature)
M (molar) mM (millimolar)
μM (micromolar) nM (nanomolar)
mol (moles) mmol (millimoles)
min (minutes) h (hours)
MeO H (methanol) EtOH (ethanol)
DCM (dichloromethane) THF (tetrahydrofuran)
EtOAc (ethyl acetate) $Ac_2O$ (acetic anhydride)
TEA (triethlamine) $K_2CO_3$ (potassium carbonate)
Pd/C (Palladium on Carbon) BnBr (benzyl bromide)
DMAP (4-dimethylaminopyridine) KI (potassium iodide)
$Na_2C_3O$ (sodium carbonate) $Na_2SO_4$ (sodium sulfate)

Preparation of Compounds of the Present Disclosure

Below, the illustrating synthetic examples of some compounds of the present disclosure are described, and other compounds can be prepared by the similar method to one described below with different starting or reacting materials.

Scheme 1

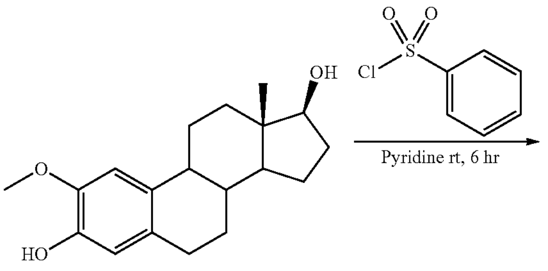

-continued

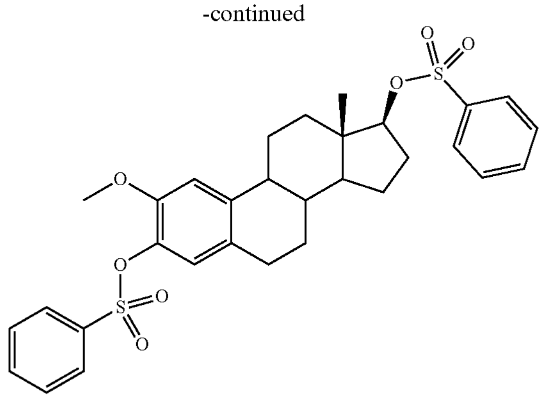

A

General Procedure for the Synthesis of A

To a stirred solution of 2-Methoxyestradiol (0.99 mmol) in pyridine (2 mL) were added benzenesulfonyl chloride (4.96 mmol) and the mixture was stirred for 6 hours at room temperature. After the reaction was completed, the reaction mixture was poured to the water and then extracted with EtOAc (15 mL) several times. The combined organic layer was washed with brine (10 mL), dried over $Na_2SO_4$, filtered and concentrated in vacuo. The resulting crude residue was purified by flash column chromatography to give A.

Scheme 2

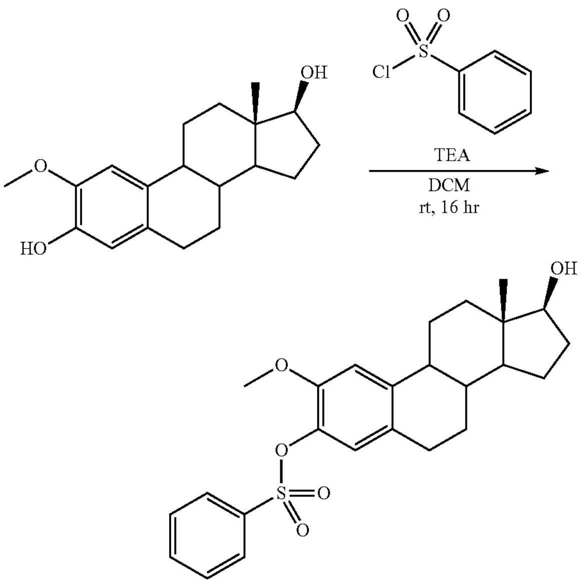

B

General Procedure for the Synthesis of B

To a stirred solution of 2-Methoxyestradiol (0.99 mmol) in anhydrous DCM (2 mL) were added TEA (9.92 mmol), benzenesulfonyl chloride (4.96 mmol) and the mixture was stirred for 16 hours at room temperature. After the reaction was completed, the reaction mixture was poured to the water and then extracted with DCM (15 mL) several times. The combined organic layer was washed with brine (10 mL), dried over $Na_2SO_4$, filtered and concentrated in vacuo. The resulting crude residue was purified by flash column chromatography to give B.

Scheme 3

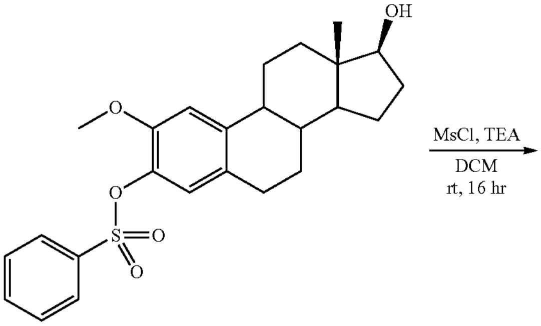

B

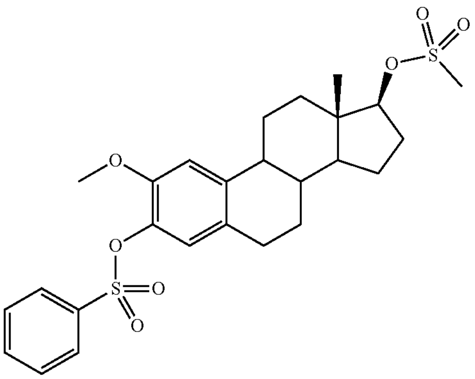

C

General Procedure for the Synthesis of C

To a stirred solution of B (0.45 mmol) in anhydrous DCM (5 mL) were added trimethylamine (1.36 mmol), Methanesulfonyl chloride (0.90 mmol) and the mixture was stirred for 16 hours at room temperature. After the reaction was completed, the reaction mixture was poured to the water and then extracted with DCM (15 mL) several times. The combined organic layer was washed with brine (10 mL), dried over $Na_2SO_4$, filtered and concentrated in vacuo. The resulting crude residue was purified by flash column chromatography to give C.

Scheme 4

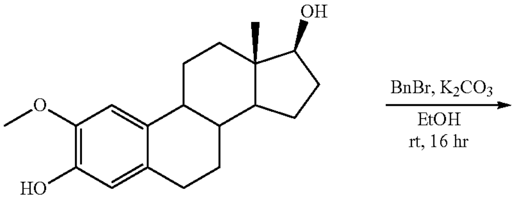

-continued

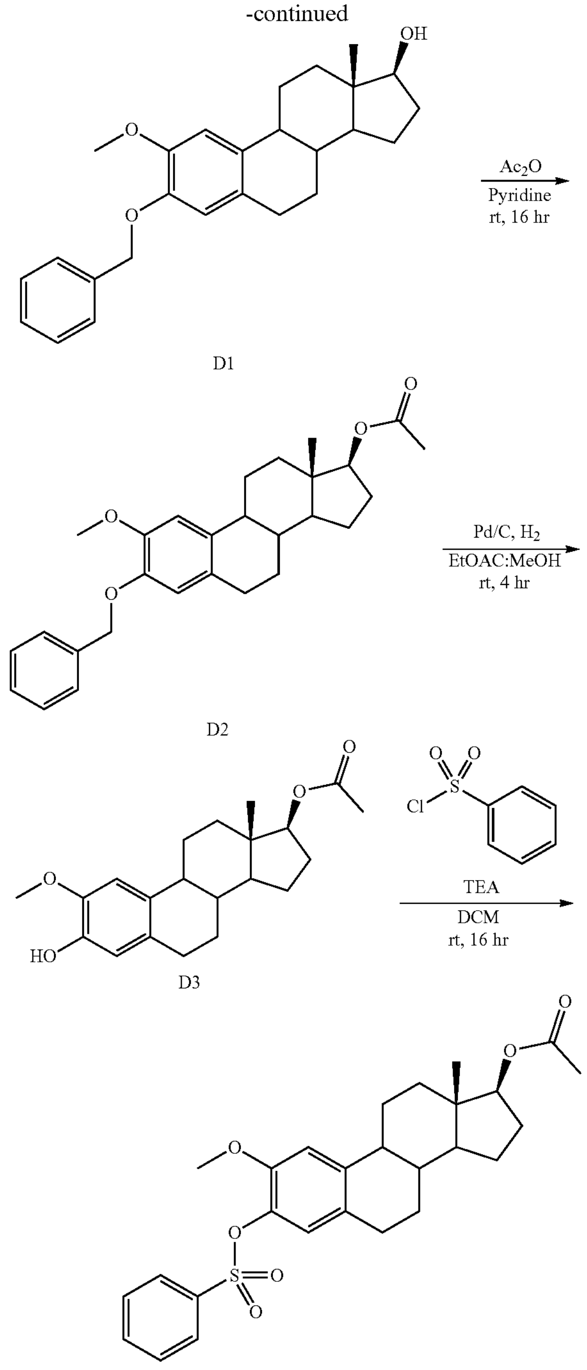

D1 D2 D3 D4

General Procedure for the Synthesis of D1

To a stirred solution of 2-Methoxyestradiol (16.53 mmol) in EtOH (100 mL) were potassium carbonate (49.60 mmol), BnBr (49.60 mmol) and the mixture was stirred for 16 hours at room temperature. After the reaction was completed, the reaction mixture was concentrated and then dissolved in EtOAc. The organic solution was washed with aqueous $Na_2CO_3$ (sat. 100 mL) and brine (10 mL), dried over $Na_2SO_4$, filtered and concentrated in vacuo. The resulting crude residue was purified by flash column chromatography to give D1.

Pale yellow solid; 1H NMR (400 MHz, Acetone-$d_6$) δ 7.48 (d, J=7.6 Hz, 2H), 7.39 (t, J=2.8 Hz, 2H), 7.33-7.29 (m, 1H), 6.90 (s, 1H), 5.06 (s, 2H), 3.79 (s, 1H), 3.75-3.65 (m, 1H), 3.56 (d, J=5.2 Hz, 1H); LCMS (ESI) m/z 583 $(M+H)^+$.

General Procedure for the Synthesis of D2

To a stirred solution of D1 (1.27 mmol) in pyridine (5 ml) were added $Ac_2O$ (6.37 mmol) and the mixture was stirred for 16 hours at room temperature. After the reaction was completed, the reaction mixture was poured to the water and then extracted with EtOAc (15 mL) several times. The combined organic layer was washed with brine (10 mL), dried over $Na_2SO_4$, filtered and concentrated in vacuo. The resulting crude residue was purified by flash column chromatography to give D2.

White solid; 1H NMR (400 MHz, Acetone-$d_6$) δ 7.48 (d, J=7.2 Hz, 2H), 7.38 (t, J=7.2 Hz, 2H), 7.37-7.29 (m, 1H), 6.89 (s, 1H), 6.73 (s, 1H), 5.06 (s, 2H), 4.67 (t, J=7.6 Hz, 1H), 3.80 (s, 3H), 2.89-2.73 (m, 3H), 2.38-2.30 (m, 1H), 2.27-2.12 (m. 2H), 1.97 (s, 3H), 1.91-1.83 (m, 2H), 1.80-1.71 (m, 1H), 1.60-1.51 (m, 1H), 1.50-1.39 (m, 5H), 1.38-1.28 (m, 3H), 0.86 (s, 3H); LCMS (ESI) m/z 435 $(M+H)^+$.

General Procedure for the Synthesis of D3

To a stirred solution of D2 (0.83 mmol) in a mixture of EtOAc and MeOH (3:1 ratio, 4 mL) were added 10% Pd/C (30 mg) and the resulting solution under $H_2$ for 4 hours at room temperature. After the reaction was completed, the palladium was filtered off by silica and the filtrate was concentrated in vacuo. The resulting crude residue was purified by flash column chromatography to give D3.

Pale yellow solid; 1H NMR (400 MHz, Acetone-$d_6$) δ 7.19 (brs, 1H), 6.85 (s, 1H), 6.52 (s, 1H), 4.66 (t, J=8.4 Hz, 1H), 3.80 (s, 3H), 2.77-2.60 (m, 2H), 2.47-2.28 (m, 1H), 2.26-2.12 (m. 2H), 2.00 (s, 3H), 1.92-1.83 (m, 2H), 1.81-1.73 (m, 1H), 1.60-1.52 (m, 1H), 1.50-1.40 (m, 4H), 1.38-1.26 (m, 3H), 0.86 (s, 3H); LCMS (ESI) m/z 345 $(M+H)^+$.

General Procedure for the Synthesis of D4

To a stirred solution of D3 (0.17 mmol) in anhydrous DCM (2 mL) were added TEA (0.52 mmol), benzenesulfonyl chloride (0.348 mmol) and the mixture was stirred for 16 hours at room temperature. After the reaction was completed, the reaction mixture was poured to the water and then extracted with DCM (15 mL) several times. The combined organic layer was washed with brine (10 mL), dried over $Na_2SO_4$, filtered and concentrated in vacuo. The resulting crude residue was purified by flash column chromatography to give D4.

White solid; 1H NMR (400 MHz, Acetone-$d_6$) δ 7.87 (d, J=7.6 Hz, 2H), 7.79 (t, J=7.2 Hz, 1H), 7.66 (t, J=7.6 Hz, 2H), 6.90 (s, 1H), 6.83 (s, 1H), 4.66 (t, J=8.4 Hz, 1H), 3.50 (s, 3H), 2.76-2.70 (m, 2H), 2.60-2.30 (m, 1H), 2.20-2.15 (m, 2H), 1.99 (s, 3H), 1.87-1.83 (m, 2H), 1.77-1.73 (m, 1H), 1.55-1.30 (m 9H), 0.86 (s, 3H); LCMS (ESI) m/z 485 $(M+H)^+$.

Structures and characteristics of the compounds according to the present disclosure and some comparative examples are written in Table 2 below.

TABLE 2

| No. | structure | Name | NMR Characterization |
|---|---|---|---|
| 1 | 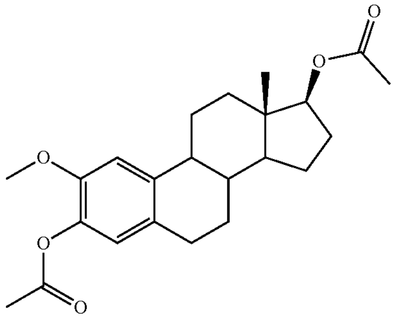 [SMILES: COc1cc2c(cc1OC(C)=O)CCC1C2CC[C@@]2(C)C1CC[C@@H]2OC(C)=O] | (13S,17S)-2-methoxy-13-methyl-7,8,9,11,12,13,14,15,16,17-decahydro-6H-cyclopenta[a]phenanthrene-3,17-diyl diacetate | White solid; $^1H$ NMR (400 MHz, Acetone-$d_6$) δ 6.98 (s, 1H), 6.71 (s, 1H), 4.67 (t, J = 8.8 Hz, 1H), 3.78 (s, 3H), 2.76-2.70 (m, 2H), 2.38-2.32 (m, 1H), 2.28-2.23 (m, 1H), 2.22 (s, 3H), 2.18-2.11 (m, 1H), 2.00 (s, 3H), 1.93-1.83 (m, 2H), 1.82-1.75 (m, 1H), 1.59-1.28 (m 9H), 0.87 (s, 3H); LCMS (ESI) m/z 387 $(M + H)^+$. |
| 2 | 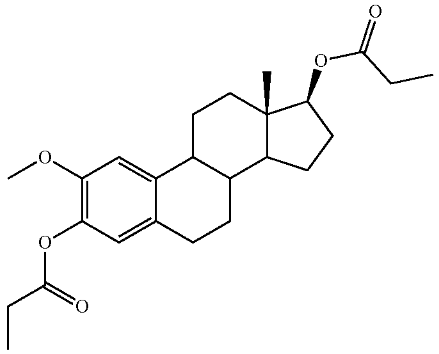 [SMILES: CCC(=O)Oc1cc2c(cc1OC)C1CC[C@@]3(C)C(CC[C@@H]3OC(=O)CC)C1CC2] | (13S,17S)-2-methoxy-13-methyl-7,8,9,11,12,13,14,15,16,17-decahydro-6H-cyclopenta[a]phenanthrene-3,17-diyl dipropionate | White solid; $^1H$ NMR (400 MHz, Acetone-$d_6$) δ 6.98 (s, 1H), 6.71 (s, 1H), 4.67 (t, J = 8.8 Hz, 1H), 3.77 (s, 3H), 2.80-2.73 (m, 2H), 2.54 (q, J = 7.2 Hz, 2H), 2.50-2.15 (m, 6H), 1.95-1.85 (m, 2H), 1.83-1.74 (m, 1H), 1.60-1.30 (m, 9H), 1.19 (t, J = 7.6 Hz, 3H), 1.10 (t, J = 7.6 Hz, 3H), 0.88 (s, 3H); LCMS (ESI) m/z 415 $(M + H)^+$. |
| 3 | 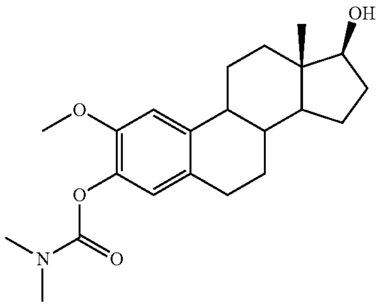 [SMILES: COc1cc2c(cc1OC(=O)N(C)C)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl dimethylcarbamate | White solid; $^1H$ NMR (400 MHz, Acetone-$d_6$) δ 6.95 (s, 1H), 6.71 (s, 1H), 3.78 (s, 3H), 3.68 (t, J = 8.4 Hz, 1H), 3.07 (s, 3H), 2.93 (s, 3H), 2.38-2.32 (m, 1H), 2.26-2.15 (m, 1H), 2.03-1.83 (m, 3H), 1.72-1.64 (m, 1H), 1.55-1.16 (m, 9H), 0.80 (s, 3H); LCMS (ESI) m/z 374 $(M + H)^+$. |
| 4 | 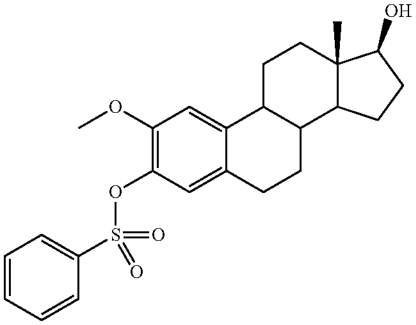 [SMILES: COc1cc2c(cc1OS(=O)(=O)c1ccccc1)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl benzenesulfonate | White solid; $^1H$ NMR (400 MHz, Acetone-$d_6$) δ 7.87 (d, J = 7.6 Hz, 2H), 7.78 (t, J = 7.6 Hz, 1H), 7.65 (t, J = 8.0 Hz, 2H), 6.89 (s, 1H), 6.81 (s, 1H), 3.66 (t, J = 7.6 Hz, 1H), 3.60 (brs, 1H), 3.50 (s, 3H), 2.76-2.31 (m, 2H), 2.31-2.21 (m, 1H), 2.28-2.15 (m, 1H), 2.06-1.85 (m, 3H), 1.70-1.62 (m, 1H), 1.54-1.15 (m 9H), 0.78 (s, 3H); LCMS (ESI) m/z 443 $(M + H)^+$. |

TABLE 2-continued

| No. | structure | Name | NMR Characterization |
|---|---|---|---|
| 5 | 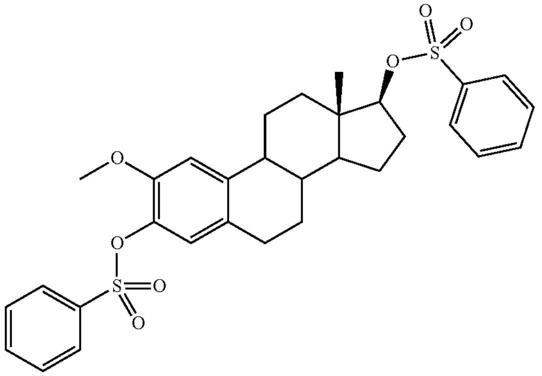 [SMILES: COc1cc2c(cc1OS(=O)(=O)c1ccccc1)CCC1C2CC[C@@]2(C)C1CC[C@@H]2OS(=O)(=O)c1ccccc1] | (13S,17S)-2-methoxy-13-methyl-7,8,9,11,12,13,14,15,16,17-decahydro-6H-cyclopenta[a]phenanthrene-3,17-diyl dibenzenesulfonate | White solid; $^{1}$H NMR (400 MHz, Acetone-$d_6$) δ 7.94-7.87 (m, 2H), 7.86-7.80 (m, 2H), 7.79-7.76 (m, 2H), 7.70-7.62 (m, 4H), 6.86 (s, 1H), 6.80 (s, 1H), 4.42 (t, J = 8.8 Hz, 1H), 3.49 (s, 3H), 2.79-2.73 (m, 2H), 2.71-2.19 (m, 2H), 2.01-1.96 (m, 1H), 1.83-1.73 (m, 1H), 1.72-1.63 (m, 3H), 1.45-1.34 (m 3H), 1.33-1.21 (m, 3H), 1.15-1.11(m, 1H), 0.84 (s, 3H); LCMS (ESI) m/z 583 $(M + H)^+$. |
| 6 | 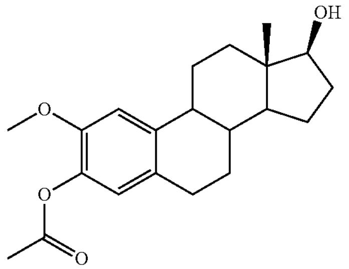 [SMILES: COc1cc2c(cc1OC(C)=O)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl acetate | White solid; $^{1}$H NMR (400 MHz, Acetone-$d_6$) δ 6.98 (s, 1H), 6.70 (s, 1H), 3.82 (s, 3H), 3.72-3.65 (m, 1H), 3.59 (d, J = 4.8 Hz, 1H), 2.77-2.72 (m, 2H), 2.38-2.32 (m, 1H), 2.21 (s, 3H), 2.03-1.92 (m, 2H), 1.91-1.83 (m, 1H), 1.73-1.64 (m, 1H), 1.55-1.15 (m, 9H), 0.80 (s, 3H); LCMS (ESI) m/z 345 $(M + H)^+$. |
| 7 | 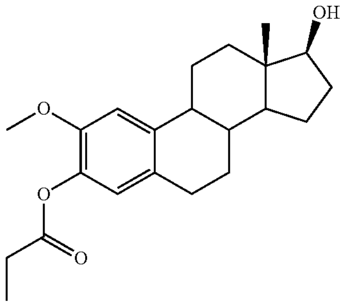 [SMILES: CCC(=O)Oc1cc2c(cc1OC)C1CC[C@@]3(C)C(CC[C@@H]3O)C1CC2] | (13S,17S)-17-hydroxy-2-methoxy-13-methyl-7,8,9,11,12,13,14,15,16,17-decahydro-6H-cyclopenta[a]phenanthren-3-yl propionate | White solid; $^{1}$H NMR (400 MHz, Acetone-$d_6$) δ 6.98 (s, 1H), 6.70 (s, 1H), 3.77 (s, 3H), 3.68 (t, J = 8.4 Hz, 1H), 3.60 (brs, 1H), 2.78-2.72 (m, 2H), 2.54 (t, J = 7.2 Hz, 2H), 2.38-2.31 (m, 1H), 2.25-2.16 (m, 1H), 2.07-1.92 (m, 2H), 1.91-1.84 (m, 1H), 1.72-1.64 (m, 1H), 1.55-1.23 (m, 8H), 1.17 (t, J = 8.0 Hz, 1H), 0.80 (s, 3H); LCMS (ESI) m/z 359 $(M + H)^+$. |
| 8 | 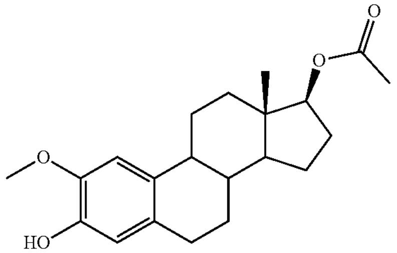 [SMILES: COc1cc2c(cc1O)CCC1C2CC[C@@]2(C)C1CC[C@@H]2OC(C)=O] | (13S,17S)-3-hydroxy-2-methoxy-13-methyl-7,8,9,11,12,13,14,15,16,17-decahydro-6H-cyclopenta[a]phenanthren-17-yl acetate | Pale yellow solid; $^{1}$H NMR (400 MHz, Acetone-$d_6$) δ 7.19 (brs, 1H), 6.85 (s, 1H), 6.52 (s, 1H), 4.66 (t, J = 8.4 Hz, 1H), 3.80 (s, 3H), 2.77-2.60 (m, 2H), 2.47-2.28 (m, 1H), 2.26-2.12 (m, 2H), 2.00 (s, 3H), 1.92-1.83 (m, 2H), 1.81-1.73 (m, 1H), 1.60-1.52 (m, 1H), 1.50-1.40 (m, 4H), 1.38-1.26 (m, 3H), 0.86 (s, 3H); LCMS (ESI) m/z 345 $(M + H)^+$. |
| 9 | 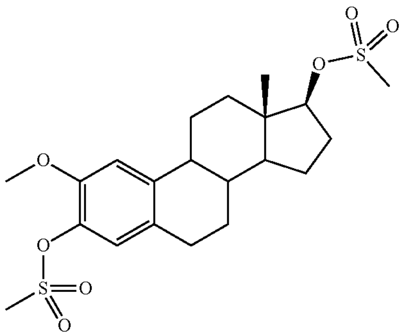 [SMILES: COc1cc2c(cc1OS(C)(=O)=O)CCC1C2CC[C@@]2(C)C1CC[C@@H]2OS(C)(=O)=O] | (13S,17S)-2-methoxy-13-methyl-7,8,9,11,12,13,14,15,16,17-decahydro-6H-cyclopenta[a]phenanthrene-3,17-diyl dimethanesulfonate | White solid; $^{1}$H NMR (400 MHz, Acetone-$d_6$) δ 7.08 (s, 1H), 6.97 (s, 1H), 4.56 (t, J = 8.4 Hz, 1H), 3.90 (s, 3H), 3.22 (s, 3H), 3.10 (s, 3H), 2.85-2.81 (m, 3H), 2.48-2.41 (m, 1H), 2.37-2.25 (m, 2H), 2.05-2.01 (m, 1H), 1.96-1.87 (m, 1H), 1.85-1.76 (m, 2H), 1.54-1.45 (m 4H), 1.41-1.33 (m, 2H), 0.90 (s, 3H); LCMS (ESI) m/z 459 $(M + H)^+$. |

TABLE 2-continued

| No. | structure | Name | NMR Characterization |
|---|---|---|---|
| 10 | 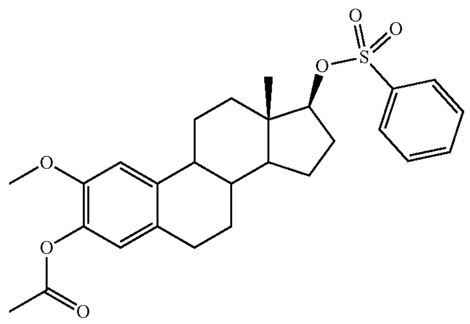 [SMILES: COc1cc2c(cc1OC(C)=O)CCC1C2CC[C@@]2(C)C1CC[C@@H]2OS(=O)(=O)c1ccccc1] | (13S,17S)-2-methoxy-13-methyl-17-((phenylsulfonyl)oxy)-7,8,9,11,12,13,14,15,16,17-decahydro-6H-cyclopenta[a]phenanthren-3-yl acetate | White solid; $^1$H NMR (400 MHz, Acetone-$d_6$) δ 7.97 (d, J = 7.6 Hz, 2H), 7.79 (t, J = 7.6 Hz, 1H), 7.70 (t, J = 8.0 Hz, 2H), 6.94 (s, 1H), 6.69 (s, 1H), 4.43 (t, J = 7.6 Hz, 1H), 3.77 (s, 3H), 2.75-2.70 (m, 2H), 2.31-2.25 (m, 1H), 2.20 (s, 3H), 2.18-2.12 (m, 1H), 2.05-1.95 (m, 1H), 1.89-1.81 (m, 1H), 1.77-1.64 (m, 3H), 1.49-1.38 (m, 3H), 1.36-1.21 (m, 2H), 1.18-1.10 (m, 1H), 0.83 (s, 3H); LCMS (ESI) m/z 485 $(M + H)^+$. |
| 11 | 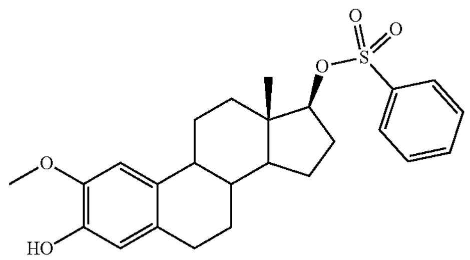 [SMILES: COc1cc2c(cc1O)CCC1C2CC[C@@]2(C)C1CC[C@@H]2OS(=O)(=O)c1ccccc1] | (13S,17S)-3-hydroxy-2-methoxy-13-methyl-7,8,9,11,12,13,14,15,16,17-decahydro-6H-cyclopenta[a]phenanthren-17-yl benzenesulfonate | Pale yellow solid; $^1$H NMR (400 MHz, Acetone-$d_6$) δ 7.97 (d, J = 7.6 Hz, 2H), 7.79 (t, J = 7.6 Hz, 1H), 7.70 (t, J = 8.0 Hz, 2H), 7.18 (s, 1H), 6.81 (s, 1H), 6.50 (s, 1H), 4.43 (t, J = 8.0 Hz, 1H), 3.79 (s, 3H), 2.72-2.68 (m, 2H), 2.27-2.18 (m, 1H), 2.17-2.10 (m, 1H), 2.00-1.95 (m, 1H), 1.86-1.77 (m, 1H), 1.75-1.63 (m, 4H), 1.45-1.35 (m, 3H), 1.30-1.18 (m, 3H), 1.18-1.08 (m 1H), 0.85 (s, 3H); LCMS (ESI) m/z 443 $(M + H)^+$. |
| 12 | 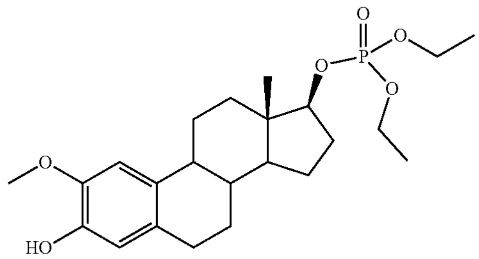 [SMILES: CCOP(=O)(OCC)O[C@H]1CCC2C3CCc4cc(O)c(OC)cc4C3CC[C@@]21C] | diethyl ((13S,17S)-3-hydroxy-2-methoxy-13-methyl-7,8,9,11,12,13,14,15,16,17-decahydro-6H-cyclopenta[a]phenanthren-17-yl) phosphate | Pale yellow solid; $^1$H NMR (400 MHz, Acetone-$d_6$) δ 7.22 (s, 1H), 6.85 (s, 1H), 6.52 (s, 1H), 4.28 (q, J = 7.6 Hz, 1H), 4.12-4.02 (m, 4H), 3.80 (s, 3H), 2.78-2.69 (m, 2H), 2.38-2.32 (m, 1H), 2.28-2.13 (m, 2H), 2.03-1.98 (m, 1H), 1.90-1.82 (m, 1H), 1.78-1.67 (m, 2H), 1.51-1.38 (m, 4H), 1.36-1.26 (m, 8H), 0.83 (s, 3H); LCMS (ESI) m/z 439 $(M + H)^+$. |
| 13 | 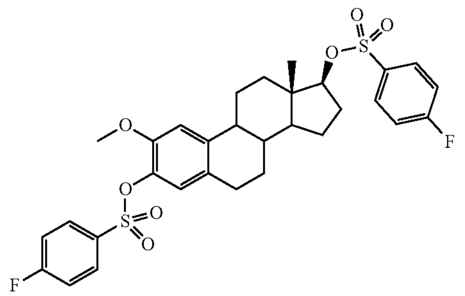 [SMILES: COc1cc2c(cc1OS(=O)(=O)c1ccc(F)cc1)CCC1C2CC[C@@]2(C)C1CC[C@@H]2OS(=O)(=O)c1ccc(F)cc1] | (13S,17S)-2-methoxy-13-methyl-7,8,9,11,12,13,14,15,16,17-decahydro-6H-cyclopenta[a]phenanthrene-3,17-diyl bis(4-fluorobenzenesulfonate) | White solid; $^1$H NMR (400 MHz, Acetone-$d_6$) δ 8.10-8.00 (m, 2H), 7.93-7.83 (m, 2H), 7.44 (q, J = 9.6, 8.8 Hz, 4H), 6.86 (d, J = 10.4 Hz, 2H), 4.43 (t, J = 7.6 Hz, 1H), 3.53 (s, 3H), 2.74-2.68 (m, 2H), 2.28-2.15 (m, 2H), 1.89-1.83 (m, 1H), 1.74-1.63 (m, 3H), 1.45-1.40 (m, 3H), 1.35-1.27 (m, 3H), 1.17-1.10 (m, 1H), 0.85 (s, 3H); LCMS (ESI) m/z 619 $(M + H)^+$. |
| 14 | 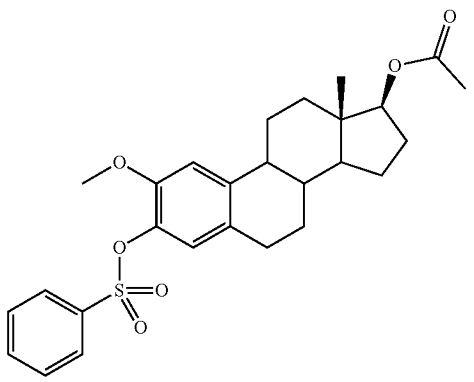 [SMILES: COc1cc2c(cc1OS(=O)(=O)c1ccccc1)CCC1C2CC[C@@]2(C)C1CC[C@@H]2OC(C)=O] | (13S,17S)-2-methoxy-13-methyl-3-((phenylsulfonyl)oxy)-7,8,9,11,12,13,14,15,16,17-decahydro-6H-cyclopenta[a]phenanthren-17-yl acetate | White solid; $^1$H NMR (400 MHz, Acetone-$d_6$) δ 7.87 (d, J = 7.6 Hz, 2H), 7.79 (t, J = 7.2 Hz, 1H), 7.66 (t, J = 7.6 Hz, 2H), 6.90 (s, 1H), 6.83 (s, 1H), 4.66 (t, J = 8.4 Hz, 1H), 3.50 (s, 3H), 2.76-2.70 (m, 2H), 2.60-2.30 (m, 1H), 2.20-2.15 (m, 2H), 1.99 (s, 3H), 1.87-1.83 (m, 2H), 1.77-1.73 (m, 1H), 1.55-1.30 (m 9H), 0.86 (s, 3H); LCMS (ESI) m/z 485 $(M + H)^+$. |

TABLE 2-continued

| No. | structure | Name | NMR Characterization |
|---|---|---|---|
| 15 | 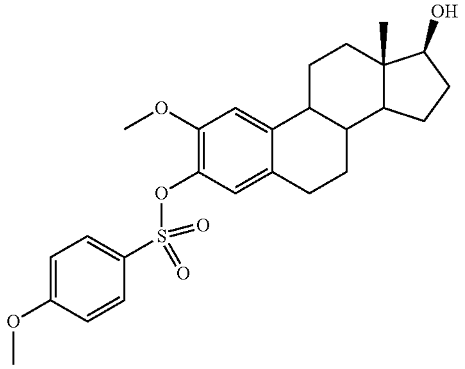 [SMILES: COc1ccc(S(=O)(=O)Oc2cc3c(cc2OC)C2CC[C@@]4(C)C(CC[C@@H]4O)C2CC3)cc1] | (13S,17S)-17-hydroxy-2-methoxy-13-methyl-7,8,9,11,12,13,14,15,16,17-decahydro-6H-cyclopenta[a]phenanthren-3-yl 4-methoxybenzenesulfonate | White solid; $^1H$ NMR (400 MHz, Acetone-$d_6$) δ 7.78 (d, J = 9.2 Hz, 2H), 7.13 (d, J = 8.8 Hz, 2H), 6.90 (s, 1H), 6.81 (s, 1H), 3.93 (s, 3H), 3.70-3.57 (m, 1H), 3.55 (s, 3H), 2.75-2.69 (m, 2H), 2.38-2.28 (m, 1H), 2.24-2.15 (m, 1H), 2.04-1.96 (m, 1H), 1.94-1.86 (m, 2H), 1.73-1.63 (m, 1H), 1.55-1.42 (m, 2H), 1.41-1.26 (m, 4H), 1.23-1.15 (m, 2H), 0.78 (s, 3H); LCMS (ESI) m/z 473 $(M + H)^+$. |
| 16 | 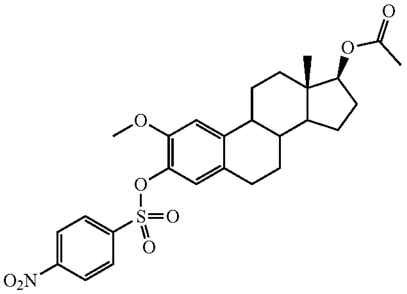 [SMILES: COc1cc2c(cc1OS(=O)(=O)c1ccc([N+](=O)[O-])cc1)CCC1C2CC[C@@]2(C)C1CC[C@@H]2OC(C)=O] | (13S,17S)-2-methoxy-13-methyl-3-(((4-nitrophenyl)sulfonyl)oxy)-7,8,9,11,12,13,14,15,16,17-decahydro-6H-cyclopenta[a]phenanthren-17-yl acetate | White solid; $^1H$ NMR (400 MHz, Acetone-$d_6$) δ 8.50 (d, J = 8.8 Hz, 2H), 8.16 (d, J = 8.8 Hz, 2H), 6.92 (s, 2H), 4.66 (t, J = 8.0 Hz, 1H), 3.50 (s, 3H), 2.78-2.73 (m, 1H), 2.45-2.25 (m, 2H), 2.24-2.12 (m, 1H), 2.00 (s, 3H), 1.95-1.85 (m, 2H), 1.84-1.73 (m, 1H), 1.59-1.40 (m, 5H), 1.39-1.30 (m, 4H), 0.86 (s, 3H); LCMS (ESI) m/z 530 $(M + H)^+$. |
| 17 | 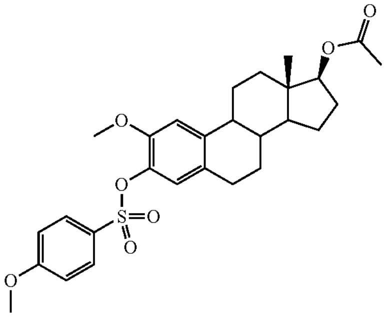 [SMILES: COc1ccc(S(=O)(=O)Oc2cc3c(cc2OC)C2CC[C@@]4(C)C(CC[C@@H]4OC(C)=O)C2CC3)cc1] | (13S,17S)-2-methoxy-3-(((4-methoxyphenyl)sulfonyl)oxy)-13-methyl-7,8,9,11,12,13,14,15,16,17-decahydro-6H-cyclopenta[a]phenanthren-17-yl acetate | White solid; $^1H$ NMR (400 MHz, Acetone-$d_6$) δ 7.78 (d, J = 8.8 Hz, 2H), 7.13 (d, J = 8.4 Hz, 2H), 6.90 (s, 1H), 6.82 (s, 1H), 4.66 (t, J = 7.6 Hz, 1H), 3.93 (s, 3H), 3.54 (s, 3H), 2.88-2.84 (m, 2H), 2.38-2.31 (m, 1H), 2.28-2.12 (m, 2H), 2.00 (s, 3H), 1.95-1.83 (m, 2H), 1.81-1.75 (m, 1H), 1.58-1.38 (m, 5H), 1.37-1.28 (m, 3H), 0.86 (s, 3H); LCMS (ESI) m/z 515 $(M + H)^+$. |
| 18 | 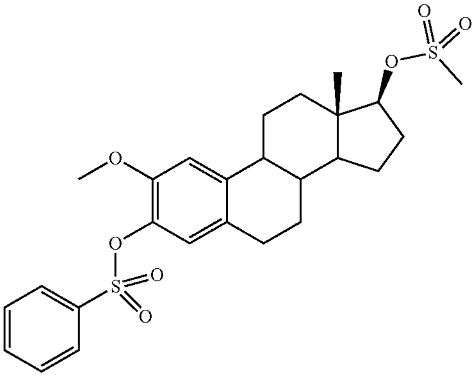 [SMILES: COc1cc2c(cc1OS(=O)(=O)c1ccccc1)CCC1C2CC[C@@]2(C)C1CC[C@@H]2OS(C)(=O)=O] | (13S,17S)-2-methoxy-13-methyl-17-((methylsulfonyl)oxy)-7,8,9,11,12,13,14,15,16,17-decahydro-6H-cyclopenta[a]phenanthren-3-yl benzenesulfonate | White solid; $^1H$ NMR (400 MHz, Acetone-$d_6$) δ 7.87 (d, J = 7.6 Hz, 2H), 7.79 (t, J = 7.6 Hz, 1H), 7.66 (t, J = 8.0 Hz, 2H), 6.91 (s, 1H), 6.83 (s, 1H), 4.57 (t, J = 7.6 Hz, 1H), 3.50 (s, 3H), 3.09 (s, 3H), 2.75-2.74 (m, 2H), 2.37-2.31 (m, 1H), 2.30-2.17 (m, 2H), 2.08-1.95 (m, 1H), 1.93-1.85 (m, 1H), 1.84-1.77 (m, 2H), 1.54-1.43 (m, 5H), 1.39-1.28 (m 3H), 0.88 (s, 3H); LCMS (ESI) m/z 521 $(M + H)^+$. |

TABLE 2-continued

| No. | structure | Name | NMR Characterization |
|---|---|---|---|
| 19 | 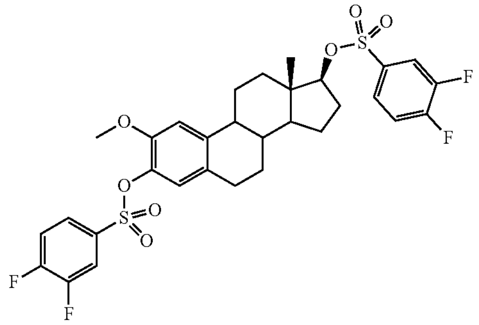 [SMILES: COc1cc2c(cc1OS(=O)(=O)c1ccc(F)c(F)c1)CCC1C2CC[C@@]2(C)C1CC[C@@H]2OS(=O)(=O)c1ccc(F)c(F)c1] | (13S,17S)-2-methoxy-13-methyl-7,8,9,11,12,13,14,15,16,17-decahydro-6H-cyclopenta[a]phenanthrene-3,17-diyl bis(3,4-difluorobenzenesulfonate) | White solid; $^{1}H$ NMR (400 MHz, Acetone-$d_6$) δ 8.03-7.91 (m, 1H), 7.90-7.78 (m, 2H), 7.76-7.69 (m, 1H), 7.65 (q, J = 9.2 Hz, 2H), 6.88 (d, J = 14.4 Hz, 2H), 4.48 (t, J = 7.6 Hz, 1H), 3.57 (s, 3H), 2.74 (d, J = 4.4 Hz, 2H), 2.25 (d, J = 13.2 Hz, 1H), 2.23-2.06 (m, 1H), 1.83 (d, J = 10.8 Hz, 1H), 1.75-1.65 (m, 3H), 1.51-1.33 (m, 3H), 1.30-1.11 (m, 4H), 0.85 (s, 3H); LCMS (ESI) m/z 655 $(M + H)^+$. |
| 20 | 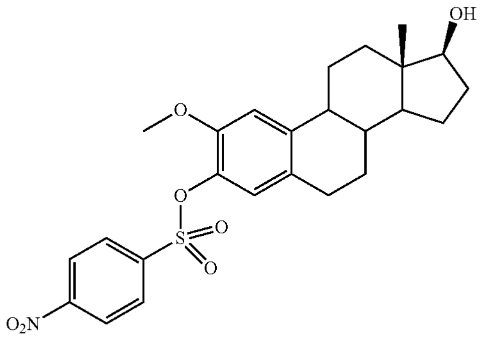 [SMILES: COc1cc2c(cc1OS(=O)(=O)c1ccc([N+](=O)[O-])cc1)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl 4-nitrobenzenesulfonate | Yellow solid; $^{1}H$ NMR (400 MHz, Acetone-$d_6$) δ 8.49 (d, J = 9.2 Hz, 2H), 8.16 (d, J = 8.8 Hz, 2H), 6.92 (s, 2H), 3.72-3.51 (m, 1H), 3.51 (s, 3H), 2.78-2.68 (m, 1H), 2.37-2.27 (m, 1H), 2.25-2.14 (m, 1H), 2.03-1.96 (m, 1H), 1.94-1.85 (m, 2H), 1.73-1.62 (m, 1H), 1.54-1.42 (m, 3H), 1.41-1.28 (m, 3H), 1.27-1.15 (m, 2H), 0.78 (s, 3H); LCMS (ESI) m/z 488 $(M + H)^+$. |
| 21 | 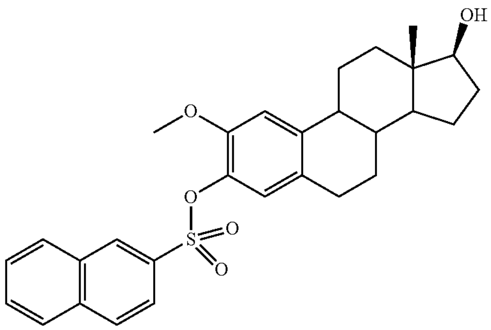 [SMILES: COc1cc2c(cc1OS(=O)(=O)c1ccc3ccccc3c1)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl naphthalene-2-sulfonate | White solid; $^{1}H$ NMR (400 MHz, 8.17 (d, J = 8.0 Hz, 2H), 8.09 (d, J = 8.0 Hz, 1H), 7.89 (dd, J = 8.4, 1.6 Hz, 1H), 7.80-7.69 (m, 2H), 6.85 (s, 2H), 3.68-3.63 (m, 1H), 3.59 (d, J = 4.8 Hz, 1H), 3.37 (s, 3H), 2.74-2.69 (m, 2H), 2.29-2.24 (m, 1H), 2.19-2.08 (m, 1H), 2.05-1.98 (m, 1H), 1.96-1.84 (m, 2H), 1.69-1.61 (m, 1H), 1.54-1.45 (m, 3H), 1.44-1.29 (m, 3H), 1.28-1.12 (m, 1H), 0.77 (s, 3H); LCMS (ESI) m/z 493 $(M + H)^+$. |
| 22 | 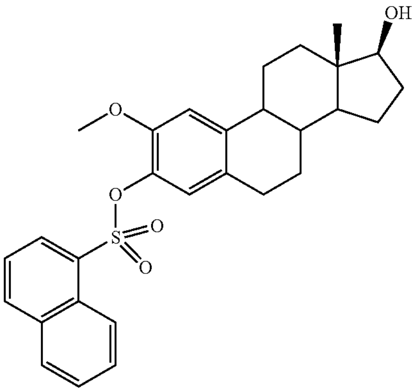 [SMILES: COc1cc2c(cc1OS(=O)(=O)c1cccc3ccccc13)CCC1C2CC[C@@]2(C)C1CC[C@@H]2O] | (13S,17S)-17-hydroxy-2-methoxy-13-methyl-7,8,9,11,12,13,14,15,16,17-decahydro-6H-cyclopenta[a]phenanthren-3-yl naphthalene-1-sulfonate | White solid; $^{1}H$ NMR (400 MHz, Acetone-$d_6$) δ 8.83 (d, J = 8.8 Hz, 1H), 8.33 (d, J = 8.8 Hz, 1H), 8.13 (td, J = 7.2, 1.2 Hz, 2H), 7.86 (td, J = 7.2, 1.6 Hz, 1H), 7.74 (td, J = 7.2, 1.2 Hz, 1H), 7.63 (t, J = 7.6 Hz, 1H), 6.80 (s, 1H), 6.72 (s, 1H), 3.68-3.62 (m, 1H), 3.60 (d, J = 4.8 Hz, 1H), 3.19 (s, 3H), 2.70-2.62 (m, 2H), 2.28-2.22 (m, 1H), 2.17-2.11 (m, 1H), 2.02-1.88 (m, 2H), 1.85-1.81 (m, 1H), 1.68-1.61 (m, 1H), 1.53-1.42 (m, 2H), 1.39-1.32 (m, 2H), 1.30-1.21 (m, 2H), 1.19-1.11 (m, 1H), 0.76 (s, 3H); LCMS (ESI) m/z 493 $(M + H)^+$. |

TABLE 2-continued

| No. | structure | Name | NMR Characterization |
|---|---|---|---|
| 23 | 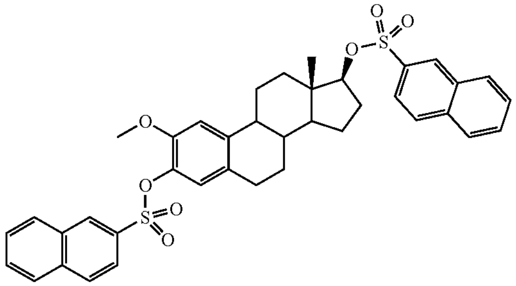 [SMILES: COc1cc2c(cc1OS(=O)(=O)c1ccc3ccccc3c1)CCC1C2CC[C@@]2(C)C1CC[C@@H]2OS(=O)(=O)c1ccc2ccccc2c1] | (13S,17S)-2-methoxy-13-methyl-7,8,9,11,12,13,14,15,16,17-decahydro-6H-cyclopenta[a]phenanthrene-3,17-diyl bis(naphthalene-2-sulfonate) | White solid; $^1H$ NMR (400 MHz, Acetone-$d_6$) δ 8.60 (s, 1H), 8.44 (s, 1H), 8.23-8.14 (m, 4H), 8.10 (t, J = 6.8 Hz, 2H), 7.93-7.86 (m, 2H), 7.79-7.69 (m, 4H), 6.82 (s, 1H), 6.77 (s, 1H), 4.45 (t, J = 8.4 Hz, 1H), 3.34 (s, 3H), 2.71-2.66 (m, 2H), 2.20-2.14 (m, 1H), 2.04-1.94 (m, 1H), 1.82-1.74 (m, 1H), 1.72-1.64 (m, 3H), 1.46-1.34 (m, 3H), 1.31-1.18 (m, 3H), 1.16-1.02 (m, 1H), 0.85 (s, 3H); LCMS (ESI) m/z 683 $(M + H)^+$. |
| 24 | 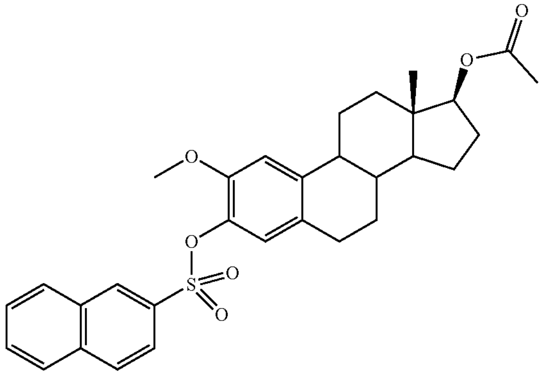 [SMILES: COc1cc2c(cc1OS(=O)(=O)c1ccc3ccccc3c1)CCC1C2CC[C@@]2(C)C1CC[C@@H]2OC(C)=O] | (13S,17S)-2-methoxy-13-methyl-3-((naphthalen-2-ylsulfonyl)oxy)-7,8,9,11,12,13,14,15,16,17-decahydro-6H-cyclopenta[a]phenanthren-17-yl acetate | White solid: $^1H$ NMR (400 MHz, Acetone-$d_6$) δ 8.46 (t, J = 0.8 Hz, 1H), 8.17 (d, J = 8.0 Hz, 2H), 8.09 (d, J = 8.0 Hz, 1H), 7.89 (dd, J = 8.8, 1.6 Hz, 1H), 7.80-7.69 (m, 2H), 6.85 (d, J = 5.6 Hz, 2H), 4.64 (t, J = 9.2 Hz, 1H), 3.36 (s, 3H), 2.78-2.71 (m, 2H), 2.29-2.26 (m, 1H), 2.24-2.14 (m, 2H), 1.98 (s, 3H), 1.96-1.84 (m, 2H), 1.78-1.73 (m, 1H), 1.55-1.46(m, 3H), 1.45-1.19 (m, 4H), 0.85 (s, 3H); LCMS (ESI) m/z 535 $(M + H)^+$. |

Evaluation of Compounds

Evaluation of 2-Methoxyestradiol (2-ME) Derivatives as Therapeutics for Radiation-Induced Pulmonary Fibrosis (RIPF)

RIPF triggers physiological abnormalities. EndMT is the phenotypic conversion of endothelial cells to fibroblast-like cells and is involved in RIPF.

We established a phenomic screening platform to measure radiation-induced stress fibers and optimized the conditions for high-throughput screening using HUVEC cells to develop compounds targeting RIPF. The results of screening indicated that 2-ME derivatives reduced radiation-induced fibrosis, as evidenced by an enlargement of cell size and increases in actin stress fibers and α-smooth muscle actin expression.

2-ME derivatives were prepared and their anti-fibrotic activities were tested in vitro [Table 3] and in vivo mouse models [FIGS. 1 and 2]. Some compounds among the total synthesized compounds showed relatively high anti-fibrotic activities on RIPF. In this test, HUVECs were pre-treated with 2-ME derivatives at 1 hour before radiation and irradiated with 10 Gy. After 48 hours, HUVECs stained with Phalloidin and Hoechst to assess morphological changes Table 3 shows validation results of in vitro efficacy of 2-ME derivatives on the RIPF

TABLE 3

| NO. | Structure | Cell number | Stress Fiber Pre- | Stress Fiber Post- |
|---|---|---|---|---|
| 1 | 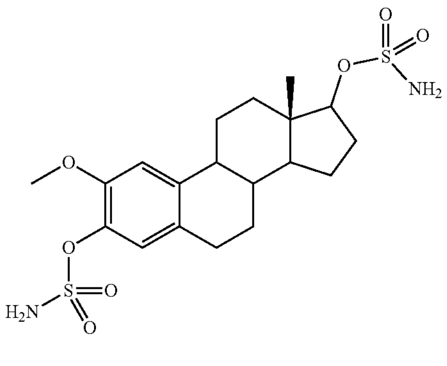 [SMILES: COc1cc2c(cc1OS(N)(=O)=O)CCC1C2CC[C@]2(C)C(OS(N)(=O)=O)CCC12] | O | X | X |

TABLE 3-continued
| NO. | Structure | Cell number | Stress Fiber Pre- | Stress Fiber Post- |
|---|---|---|---|---|
| 2 | 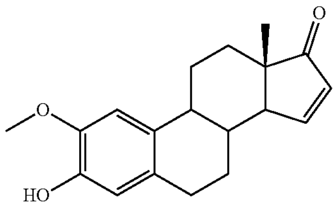 [SMILES: COc1cc2c(cc1O)CCC1C2CC[C@]2(C)C(=O)C=CC12] | X | X | X |
| 3 | 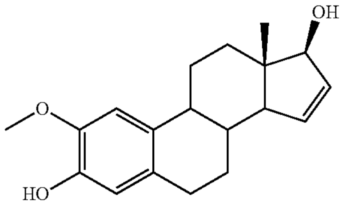 [SMILES: COc1cc2c(cc1O)CCC1C2CC[C@@]2(C)C1C=C[C@@H]2O] | O | X | X |
| 4 | 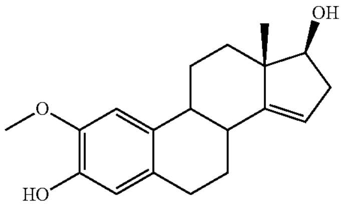 [SMILES: COc1cc2c(cc1O)CCC1C3=CC[C@H](O)[C@@]3(C)CCC21] | O | X | X |
| 5 | 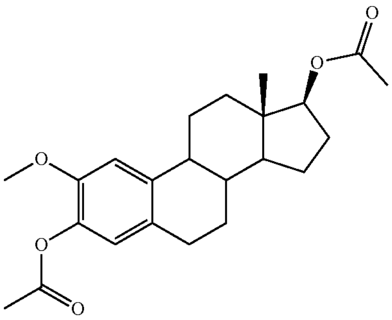 [SMILES: COc1cc2c(cc1OC(C)=O)CCC1C2CC[C@@]2(C)C1CC[C@@H]2OC(C)=O] | O | O | X |
| 6 | 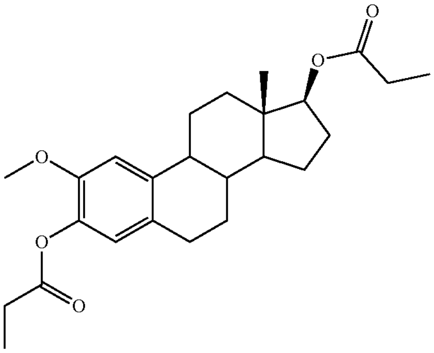 [SMILES: CCC(=O)Oc1cc2c(cc1OC)C1CC[C@@]3(C)C(CC[C@@H]3OC(=O)CC)C1CC2] | O | O | X |

TABLE 3-continued
| NO. | Structure | Cell number | Stress Fiber Pre- | Stress Fiber Post- |
|---|---|---|---|---|
| 7 | 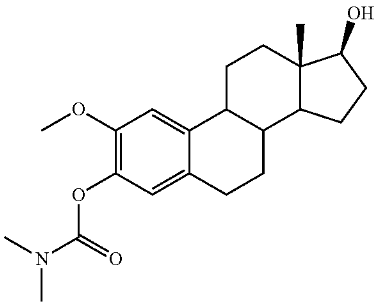 [SMILES: COc1cc2c(cc1OC(=O)N(C)C)CCC1C2CC[C@@]2(C)C1CC[C@@H]2O] | O | X | X |
| 8 | 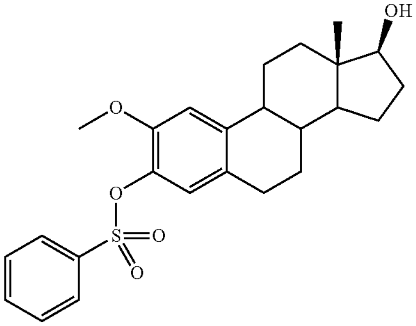 [SMILES: COc1cc2c(cc1OS(=O)(=O)c1ccccc1)CCC1C2CC[C@@]2(C)C1CC[C@@H]2O] | O | X | X |
| 9 | 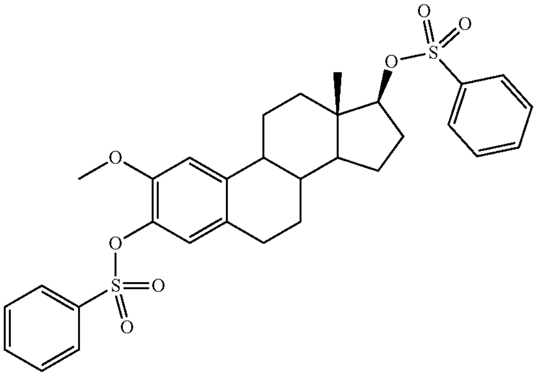 [SMILES: COc1cc2c(cc1OS(=O)(=O)c1ccccc1)CCC1C2CC[C@@]2(C)C1CC[C@@H]2OS(=O)(=O)c1ccccc1] | O | X | X |
| 10 | 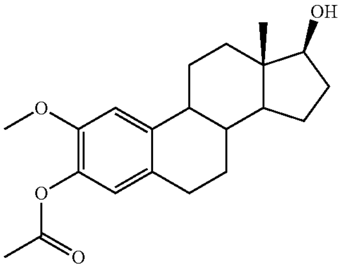 [SMILES: COc1cc2c(cc1OC(C)=O)CCC1C2CC[C@@]2(C)C1CC[C@@H]2O] | O | O | O |

TABLE 3-continued

| | | | Stress Fiber | |
|---|---|---|---|---|
| NO. | Structure | Cell number | Pre- | Post- |
| 11 | 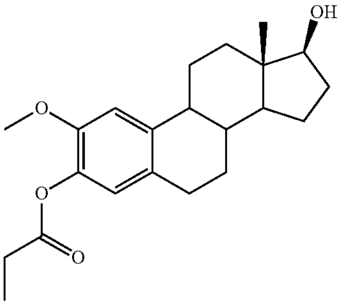 [SMILES: CCC(=O)Oc1cc2c(cc1OC)C1CC[C@@]3(C)C(CC[C@@H]3O)C1CC2] | O | O | O |
| 12 | 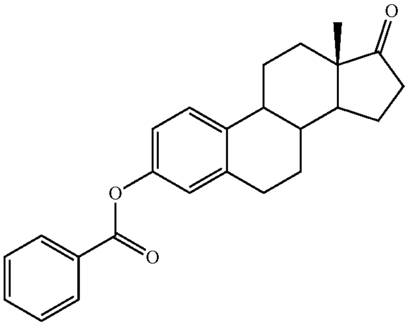 [SMILES: C[C@]12CCC3c4ccc(OC(=O)c5ccccc5)cc4CCC3C1CCC2=O] | O | X | X |
| 13 | 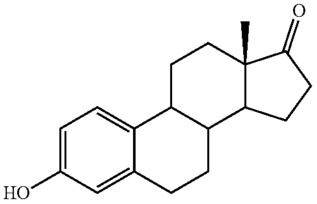 [SMILES: C[C@]12CCC3c4ccc(O)cc4CCC3C1CCC2=O] | O | X | X |
| 14 | 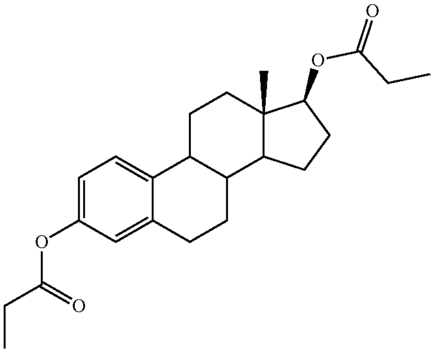 [SMILES: CCC(=O)Oc1ccc2c(c1)CCC1C2CC[C@@]2(C)C1CC[C@@H]2OC(=O)CC] | O | X | X |

*Cell number: O (there were no change in the cell number compare to IR (control) treated group), X (there were more than 10% changes in the cell number compare to IR (control) treated group)
*Stress fiber: O (there were stress fiber decreasing more than 20% compare to IR (control) treated group), X (there were no stress fiber decreasing compare to IR (control) treated group)

Materials and Methods

Validation of 2-ME Derivatives as Regulators of Radiation-Induced EndMT Using the HCS System Collagen type 1 (BD Collagen I, 354236, Thermo Fisher Scientific) was diluted in 70% ethanol, and then the collagen solution (400 μg/ml) was dispensed into each 384-well plate (6007550, Perkin Elmer, MA, US). After a 1-hour incubation at room temperature, the wells were rinsed twice with Dulbecco's phosphate-buffered saline. HUVECs were seeded at a density of $7\times10^2$ cells per well onto collagen-coated, 384-well plates and allowed to attach in complete growth media. Cells were then exposed to 10 Gy radiation at room temperature. After irradiation, the cells were incubated for an additional 3 hours. The compounds were tested at a final concentration of 10 μM in 0.5% dimethyl sulfoxide (DMSO; v/v) using an automated liquid handling system (Hummingbird, Analytik Jena, Jena, DE). After the 48-hour treatment, cells were fixed with 4% paraformaldehyde (w/v). The expression of actin filament was determined by incubation with 488-Phalloidin (1:100, MOP-A7466, Thermo Fisher Scientific) using direct immunofluorescence staining. The nuclei were stained using Hoechst 33342 (1:1000, MOP-H3570, Thermo Fisher Scientific) at room temperature. For assay validation, a control run was performed. The low control consisted of three 384-well plates that contained irradiated cells, and the high control consisted of three 384-well plates that contained non-irradiated cells. For detecting and visualizing filamentous actin (F-actin) and nuclei, images were collected using an automated high-content imaging system with a 20× magnifying objective (Operetta, PerkinElmer). The acquired images were analyzed using an in-house software tool and Harmony 3.5.1® high-content imaging (Harmony, PerkinElmer) for segmentation of cells.

Validation of In Vivo Efficacy of 2-ME Derivatives on the RIPF

Radiation was delivered using an X-RAD 320 platform (Precision X-ray). The left main bronchi of 8-week-old male C57BL/6 mice were irradiated at 90 Gy using a 4-mm diameter field to mimic an ablative dose. 1-hour prior to irradiation, 2-ME and 2-ME derivatives were injected intraperitoneally (5 per group). 2-ME and 2-ME derivatives were administered at a concentration of 30 mg/kg for 2 weeks (3 times a week). After 2 weeks of irradiation, lung tissue was harvested and fixed in 10% (v/v) neutral buffered formalin before preparing paraffin sections. Paraffin-embedded sections were deparaffinized and stained with hematoxylin and eosin (H&E; Sigma-Aldrich), and using a Masson's trichrome stain kit (Sigma-Aldrich) to detect collagen. Images were obtained using a Zeiss microscope. At least five images per section were acquired for quantification, and positively stained areas were evaluated with ImageJ software. Lung fibrosis was scored on a scale of 0 to 8 according to the following criteria: grade 0, normal lung; grade 1, minimal fibrous thickening of alveolar or bronchiolar wall; grade 2-3, moderate thickening of walls without obvious damage to lung architecture; grade 4-5, increased fibrosis with definite damage to lung architecture and formation of fibrous bands or small fibrous mass; grade 6-7, severe distortion of structure and large fibrous areas; grade 8, total fibrous obliteration of the field.

Evaluation of 2-Methoxyestradiol (2-ME) Derivatives as Therapeutics for Liver Fibrosis Despite liver fibrosis are highly prevalent disease, there are still no approved therapies because liver fibrosis has numerous causes and complications. The main causes of liver fibrosis are chronic hepatitis virus infection, alcohol abuse, drug-induced liver injury (DILI), cholestasis and NASH etc.

We evaluated activity of 2-ME derivatives as inhibitors of liver fibrosis through multicellular hepatic spheroids (MCHSs) model-based phenomic screening [Table 4] and in vivo mouse models [FIGS. 3 to 6]. Some compounds among the total synthesized compounds showed relatively high anti-fibrotic activities in liver.

Table 4 shows validation results of in vitro efficacy of 2-ME derivatives on the liver fibrosis using MCHSs.

TABLE 4

| NO. | Structure | Anti-fibrotic activity |
|---|---|---|
| 1 | 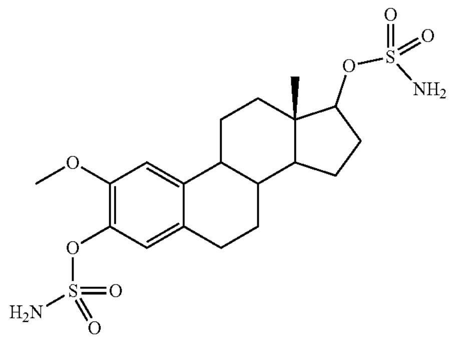 [SMILES: COc1cc2c(cc1OS(N)(=O)=O)CCC1C2CC[C@]2(C)C(OS(N)(=O)=O)CCC12] | X |
| 2 | 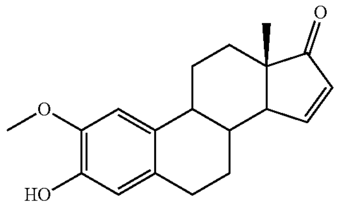 [SMILES: COc1cc2c(cc1O)CCC1C2CC[C@]2(C)C(=O)C=CC12] | X |
| 3 | 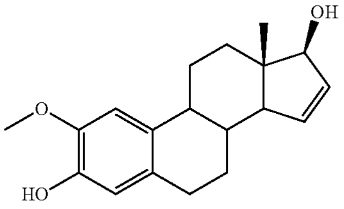 [SMILES: COc1cc2c(cc1O)CCC1C2CC[C@@]2(C)C1C=C[C@@H]2O] | X |

TABLE 4-continued
| NO. | Structure | Anti-fibrotic activity |
|---|---|---|
| 4 | 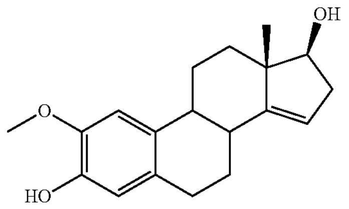 [SMILES: COc1cc2c(cc1O)CCC1C3=CC[C@H](O)[C@@]3(C)CCC21] | X |
| 5 | 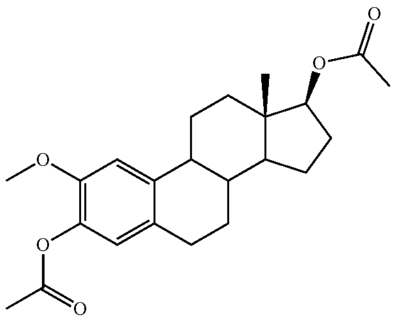 [SMILES: COc1cc2c(cc1OC(C)=O)CCC1C2CC[C@@]2(C)C1CC[C@@H]2OC(C)=O] | X |
| 6 | 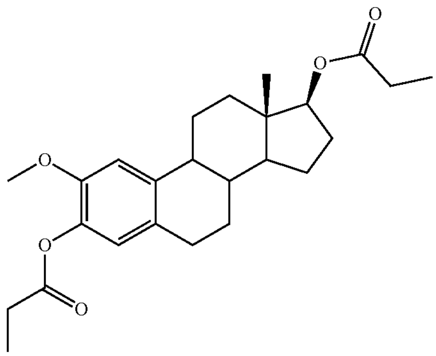 [SMILES: CCC(=O)Oc1cc2c(cc1OC)C1CC[C@@]3(C)C(CC[C@@H]3OC(=O)CC)C1CC2] | X |
| 7 | 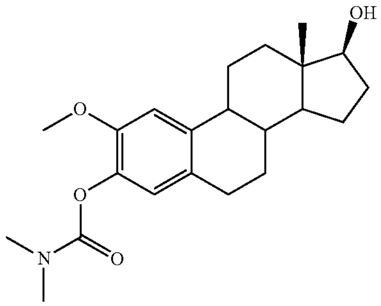 [SMILES: COc1cc2c(cc1OC(=O)N(C)C)CCC1C2CC[C@@]2(C)C1CC[C@@H]2O] | O |
| 8 | 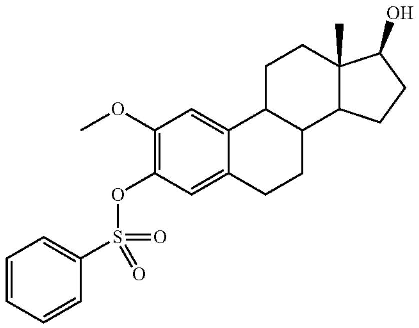 [SMILES: COc1cc2c(cc1OS(=O)(=O)c1ccccc1)CCC1C2CC[C@@]2(C)C1CC[C@@H]2O] | O |

TABLE 4-continued
| NO. | Structure | Anti-fibrotic activity |
|---|---|---|
| 9 | 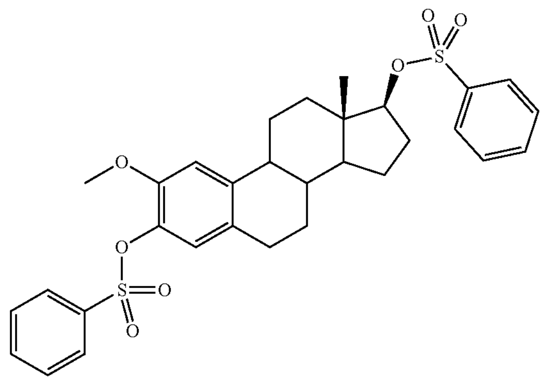 [SMILES: COc1cc2c(cc1OS(=O)(=O)c1ccccc1)CCC1C2CC[C@@]2(C)C1CC[C@@H]2OS(=O)(=O)c1ccccc1] | O |
| 10 | 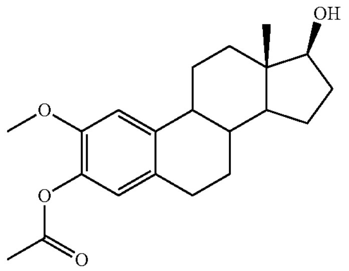 [SMILES: COc1cc2c(cc1OC(C)=O)CCC1C2CC[C@@]2(C)C1CC[C@@H]2O] | X |
| 11 | 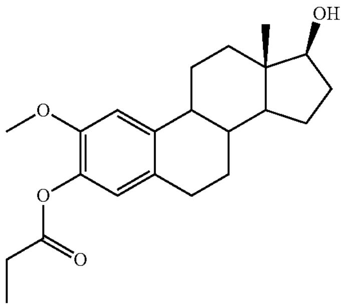 [SMILES: CCC(=O)Oc1cc2c(cc1OC)C1CC[C@@]3(C)C(CC[C@@H]3O)C1CC2] | X |
| 12 | 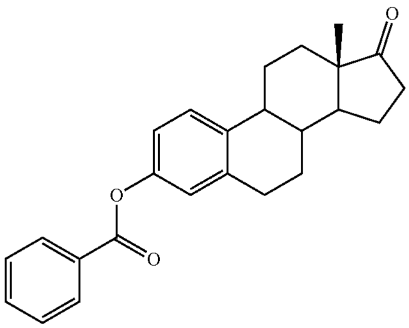 [SMILES: C[C@]12CCC3c4ccc(OC(=O)c5ccccc5)cc4CCC3C1CCC2=O] | X |
| 13 | 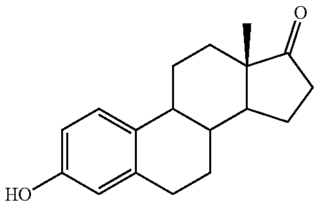 [SMILES: C[C@]12CCC3c4ccc(O)cc4CCC3C1CCC2=O] | X |

TABLE 4-continued
| NO. | Structure | Anti-fibrotic activity |
| --- | --- | --- |
| 14 | 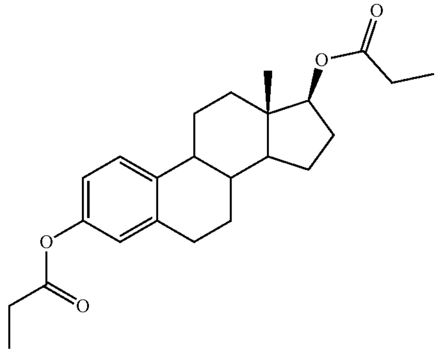 [SMILES: CCC(=O)Oc1ccc2c(c1)CCC1C2CC[C@@]2(C)C1CC[C@@H]2OC(=O)CC] | X |
| 15 | 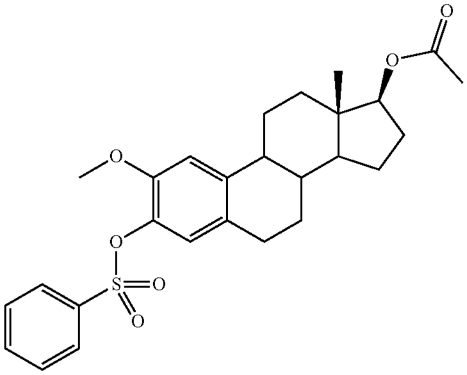 [SMILES: COc1cc2c(cc1OS(=O)(=O)c1ccccc1)CCC1C2CC[C@@]2(C)C1CC[C@@H]2OC(C)=O] | X |
| 16 | 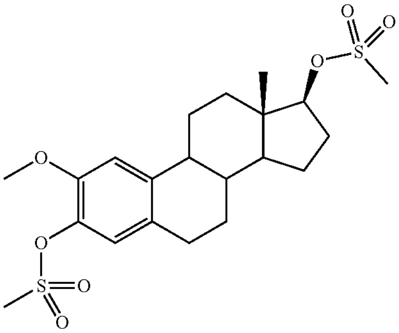 [SMILES: COc1cc2c(cc1OS(C)(=O)=O)CCC1C2CC[C@@]2(C)C1CC[C@@H]2OS(C)(=O)=O] | X |
| 17 | 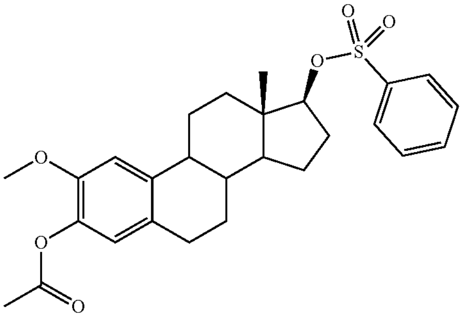 [SMILES: COc1cc2c(cc1OC(C)=O)CCC1C2CC[C@@]2(C)C1CC[C@@H]2OS(=O)(=O)c1ccccc1] | O |

TABLE 4-continued

| NO. | Structure | Anti-fibrotic activity |
| --- | --- | --- |
| 18 | 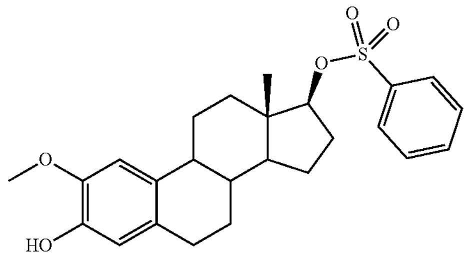 [SMILES: COc1cc2c(cc1O)CCC1C2CC[C@@]2(C)C1CC[C@@H]2OS(=O)(=O)c1ccccc1] | X |
| 19 | 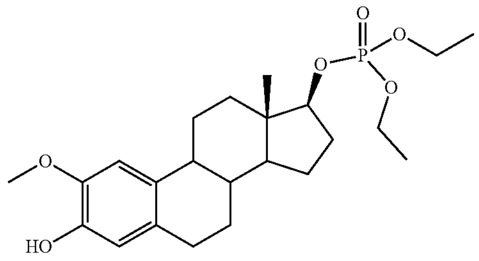 [SMILES: CCOP(=O)(OCC)O[C@H]1CCC2C3CCc4cc(O)c(OC)cc4C3CC[C@@]21C] | X |
| 20 | 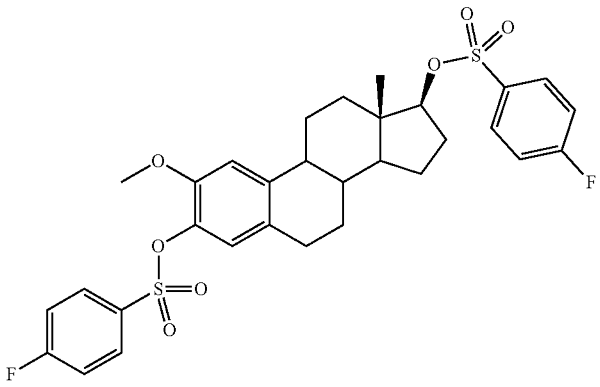 [SMILES: COc1cc2c(cc1OS(=O)(=O)c1ccc(F)cc1)CCC1C2CC[C@@]2(C)C1CC[C@@H]2OS(=O)(=O)c1ccc(F)cc1] | X |

*Anti-fibrotic activity: O (there were dimeter or size increasing compare to 2-ME (control)), X (there no dimeter or size change compare to 2-ME (control))

Materials and Methods

Validation of In Vitro Efficacy of 2-ME and it's Derivatives in 3D Fibrosis Model Huh? (hepatocellular carcinoma cell), LX2 (hepatic stellate cell), WI38 (fibroblast cell), and HUVEC (endothelial cell) were seeded on 96-well ULA U-bottom plate (Corning, 7007) at density of 6,000cells/well with 5.5:1.5:1.5:1.5 ratio. Spheroid was cultivated for 3 days, and 2-ME or 2-ME derivatives were treated for further 2 days from 10 uM to 39 nM concentration (9-points, 2-fold dilution from 10 uM). After 2 days incubation, spheroids were captured with automated high-content imaging system with a 10× magnifying objective (Operetta, PerkinElmer). Size of spheroids were analyzed using an in-house software tool and Harmony 3.5.1® high-content imaging (Harmony, PerkinElmer) for segmentation of cells. Increased dimeter of spheroids compared to 0.5% DMSO were selected as hit compounds.

$CCl_4$ Model of Liver Fibrosis 9 week old C57BL/6 male mice (CentralLab) were dosed 8 times with 1 mg/kg $CCl_4$ (Sigma) diluted olive oil for a total of 4 weeks. 2-ME, MC-011, or MC-015 were injected intraperitoneally at a concentration of 30 mg/kg (three times) or 60 mg/kg (two times) for 2 weeks. After 2 weeks of injection, liver tissue was harvested and fixed in 10% (v/v) neutral buffered formalin before preparing paraffin sections. Paraffin-embedded sections were deparaffinized and stained with hematoxylin and eosin (H&E; Sigma-Aldrich), and using a Masson's trichrome stain kit (Sigma-aldrich) to detect collagen. Images were obtained using a Zeiss microscope. At least five images per section were acquired for quantification, and positively stained areas were evaluated with ImageJ software.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

The invention claimed is:

1. A compound or pharmaceutically acceptable salt thereof, wherein the compound is (13S, 17S)-17-hydroxy- 2-methoxy-13-methyl-7,8,9,11,12,13,14,15,16,17-decahydro-6H-cyclopenta[a]phenanthren-3-yl benzenesulfonate, (13S,17S)-2-methoxy-13-methyl-7,8,9,11,12,13,14,15,16,17-decahydro-6H-cyclopenta[a]phenanthrene-3,17-diyldibenzenesulfonate, (13S,17S)-2-methoxy-13-methyl-7,8,9,11,12,13,14,15,16,17-decahydro-6H-cyclopenta[a]phenanthrene-3,17-diyl bis(4-fluorobenzenesulfonate), (13S,17S)-2-methoxy-13-methyl-3-((phenylsulfonyl)oxy)-7,8,9,11,12,13,14,15,16,17-decahydro-6H-cyclopenta[a]phenanthren-17-yl acetate, (13S,17S)-2-methoxy-13-methyl-17-((methylsulfonyl)oxy)-7,8,9,11,12,13,14,15,16,17-decahydro-6H-cyclopenta[a]phenanthren-3-yl benzenesulfonate, (13S,17S)-2-methoxy-13-methyl-7,8,9,11,12,13,14,15,16,17-decahydro-6H-cyclopenta[a]phenanthrene-3,17-diyl bis(3,4-difluorobenzenesulfonate), (13S,17S)-17-hydroxy-2-methoxy-13-methyl-7,8,9,11,12,13,14,15,16,17-decahydro-6H-cyclopenta[a]phenanthren-3-yl4-nitrobenzenesulfonate, (13S,17S)-17-hydroxy-2-methoxy-13-methyl-7,8,9,11,12,13,14,15,16,17-decahydro-6H-cyclopenta[a]phenanthren-3-yl4-methoxybenzenesulfonate, (13S,17S)-17-hydroxy-2-methoxy-13-methyl-7,8,9,11,12,13,14,15,16,17-decahydro-6H-cyclopenta[a]phenanthren-3-yl naphthalene-2-sulfonate, (13S,17S)-17-hydroxy-2-methoxy-13-methyl-7,8,9,11,12,13,14,15,16,17-decahydro-6H-cyclopenta[a]phenanthren-3-yl naphthalene-1-sulfonate, (13S,17S)-2-methoxy-13-methyl-7,8,9,11,12,13,14,15,16,17-decahydro-6H-cyclopenta[a]phenanthrene-3,17-diyl bis(naphthalene-2-sulfonate), (13S,17S)-2-methoxy-13-methyl-3-((naphthalen-2-ylsulfonyl)oxy)-7,8,9,11,12,13,14,15,16,17-decahydro-6H-cyclopenta[a]phenanthren-17-yl acetate, (13S,17S)-2-methoxy-13-methyl-7,8,9,11,12,13,14,15,16,17-decahydro-6H-cyclopenta[a]phenanthrene-3,17-diyl bis(4-fluorobenzenesulfonate), (13S,17S)-2-methoxy-13-methyl-3-(((4-nitrophenyl)sulfonyl)oxy)-7,8,9,11,12,13,14,15,16,17-decahydro-6H-cyclopenta[a]phenanthren-17-yl acetate, or (13S,17S)-2-methoxy-3-(((4-methoxyphenyl)sulfonyl)oxy)-13-methyl-7,8,9,11,12,13,14,15,16,17-decahydro-6H-cyclopenta[a]phenanthren-17-yl acetate.

2. The compound or pharmaceutically acceptable salt of claim 1, wherein the compound is (13S, 17S)-17-hydroxy-2-methoxy-13-methyl-7,8,9,11,12,13,14,15,16,17-decahydro-6H-cyclopenta[a]phenanthren-3-yl benzenesulfonate, (13S,17S)-2-methoxy-13-methyl-7,8,9,11,12,13,14,15,16,17-decahydro-6H-cyclopenta[a]phenanthrene-3,17-diyldibenzenesulfonate, (13S, 17S)-2-methoxy-13-methyl-17-((methylsulfonyl)oxy)-7,8,9,11,12,13,14,15,16,17-decahydro-6H-cyclopenta[a]phenanthren-3-yl benzenesulfonate, or (13S,17S)-2-methoxy-13-methyl-7,8,9,11,12,13,14,15,16,17-decahydro-6H-cyclopenta[a]phenanthrene-3,17-diyl bis(naphthalene-2-sulfonate).

3. A composition comprising a compound or pharmaceutically acceptable salt of claim 1 and a pharmaceutically acceptable carrier.

4. A method for treating or preventing fibrosis, comprising:

administering to a subject in need of treatment or prevention of fibrosis a compound or pharmaceutically acceptable salt of claim 1.

5. The method of claim 4, wherein the fibrosis is liver fibrosis or pulmonary fibrosis.

6. The method of claim 5, wherein the liver fibrosis is a fibrosis caused by chronic hepatitis virus infection, alcohol abuse, drug-induced liver injury (DILI), cholestasis, or NASH (Non-Alcoholic Steath Hepatitis).

* * * * *